(12) United States Patent
Sullivan et al.

(10) Patent No.: US 8,579,856 B2
(45) Date of Patent: Nov. 12, 2013

(54) UNIT DOSE DRUG DELIVERY PLATFORM

(75) Inventors: Timothy R. Sullivan, Austin, TX (US);
Jeffrey Nelson, Round Rock, TX (US)

(73) Assignee: Mystic Pharmaceuticals, Inc., Cedar Park, TX (US)

( * ) Notice: Subject to any disclaimer, the term of this patent is extended or adjusted under 35 U.S.C. 154(b) by 381 days.

(21) Appl. No.: 12/851,524

(22) Filed: Aug. 5, 2010

(65) Prior Publication Data
US 2010/0331765 A1 Dec. 30, 2010

Related U.S. Application Data

(63) Continuation-in-part of application No. 11/971,471, filed on Jan. 9, 2008, now Pat. No. 8,377,009.

(60) Provisional application No. 60/982,643, filed on Oct. 25, 2007, provisional application No. 60/978,619, filed on Oct. 9, 2007, provisional application No. 60/944,700, filed on Jun. 18, 2007, provisional application No. 60/938,379, filed on May 16, 2007, provisional application No. 61/231,587, filed on Aug. 5, 2009.

(51) Int. Cl.
*A61M 1/00* (2006.01)

(52) U.S. Cl.
USPC ............... 604/118; 604/218; 604/298

(58) Field of Classification Search
USPC ............. 128/200.14; 604/294–298, 300–301
See application file for complete search history.

(56) References Cited

U.S. PATENT DOCUMENTS

| | | | |
|---|---|---|---|
| 2,769,443 A | 11/1956 | Dunmire | |
| 4,684,366 A | 8/1987 | Denny et al. | |
| 4,798,288 A | 1/1989 | Holzner | |
| 4,852,551 A | 8/1989 | Opie et al. | |
| 5,154,710 A | 10/1992 | Williams | |
| 5,215,221 A | 6/1993 | Dirksing | |
| 5,616,128 A | 4/1997 | Meyer | |
| 6,105,761 A | 8/2000 | Peuker et al. | |
| 6,116,238 A | 9/2000 | Jackson et al. | |
| 6,708,846 B1 | 3/2004 | Fuchs et al. | |
| 6,726,665 B1 * | 4/2004 | Embleton et al. | 604/290 |
| 7,097,075 B2 | 8/2006 | Peuker et al. | |
| 7,276,029 B2 * | 10/2007 | Goode et al. | 600/365 |
| 7,669,597 B2 | 3/2010 | Sullivan et al. | |
| 7,963,089 B2 | 6/2011 | Nelson et al. | |
| 8,047,204 B2 | 11/2011 | Sullivan et al. | |

(Continued)

FOREIGN PATENT DOCUMENTS

| WO | WO 94/20408 | 9/2004 |
|---|---|---|
| WO | WO2005/032998 | 4/2005 |

(Continued)

*Primary Examiner* — Nicholas Lucchesi
*Assistant Examiner* — Melissa A Snyder
(74) *Attorney, Agent, or Firm* — Vinson & Elkins LLP

(57) ABSTRACT

The delivery systems of the present disclosure are configurable to administer either single-dose or multiple-doses of one or more substances to a user, for example to the eye, nose, mouth, ear or rectum of the user. The precise and repeatable dosing features of the presently disclosed delivery systems overcome many of the disadvantages associated with known methods for dispensing substances to, for example, the eye of a user. The delivery systems administer precise doses of a substance to a precise location from unit dosage forms that may be single-dose or multiple-dose unit dosage forms, which may be externally or internally pierced.

49 Claims, 21 Drawing Sheets

(56) References Cited

U.S. PATENT DOCUMENTS

| | | |
|---|---|---|
| 2004/0099676 A1 * | 5/2004 | Anderson et al. ............... 221/25 |
| 2004/0215133 A1 | 10/2004 | Weber et al. |
| 2008/0123465 A1 | 5/2008 | Heusser et al. |
| 2008/0177246 A1 | 7/2008 | Sullivan et al. |
| 2010/0331765 A1 | 12/2010 | Sullivan et al. |
| 2011/0247305 A1 | 10/2011 | Nelson |
| 2011/0277763 A1 | 11/2011 | Sullivan et al. |

FOREIGN PATENT DOCUMENTS

| | | |
|---|---|---|
| WO | WO2005/102058 | 11/2005 |
| WO | WO2008/086413 | 7/2008 |
| WO | WO2008/144439 | 11/2008 |
| WO | WO2009/036422 | 3/2009 |

* cited by examiner

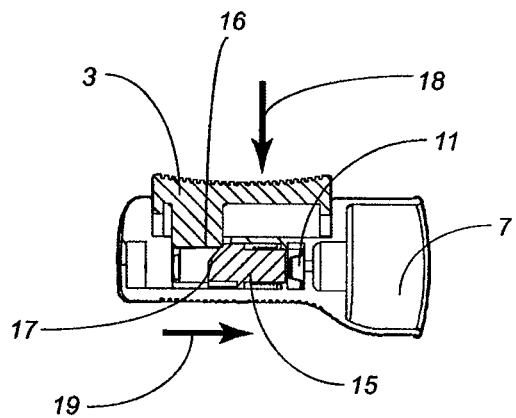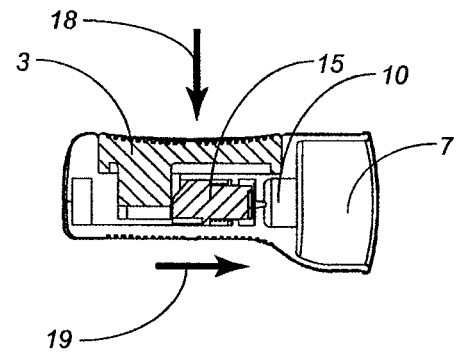
*Fig. 7a*  *Fig. 7b*
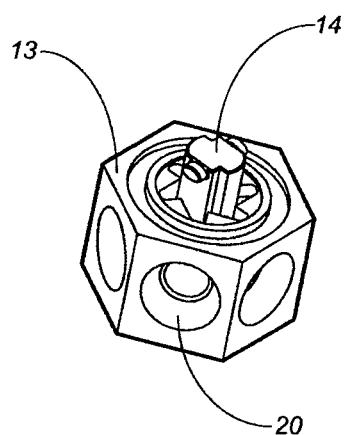
*Fig. 8*

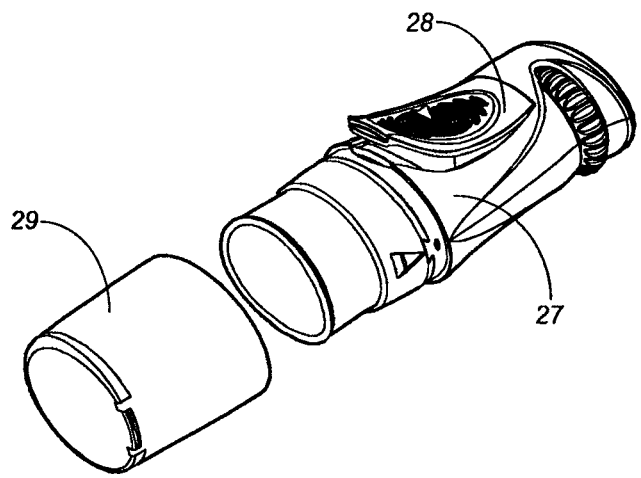
Fig. 12
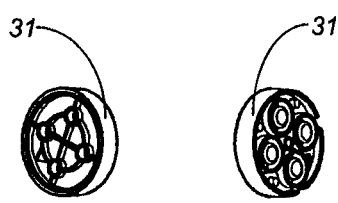
Fig. 13a  Fig. 13b

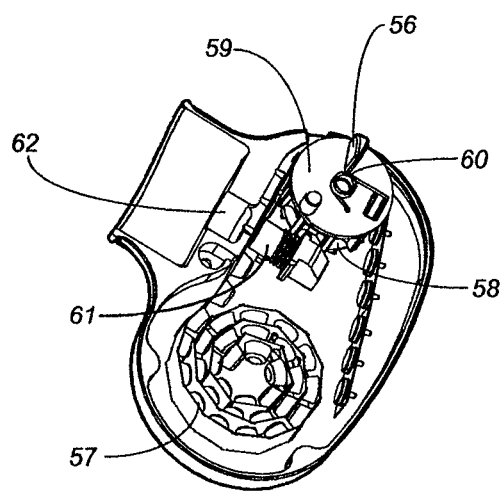
Fig. 24
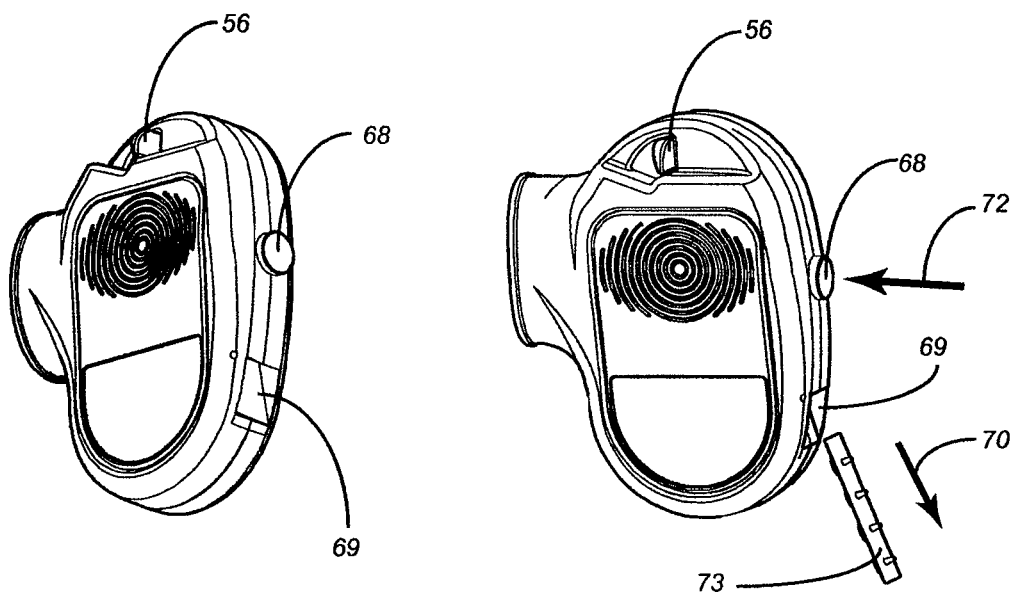
Fig. 25a  Fig. 25b

UNIT DOSE DRUG DELIVERY PLATFORM

CROSS-REFERENCE TO RELATED APPLICATIONS

This application is a continuation-in-part of U.S. Ser. No. 11/971,471, filed Jan. 9, 2008 now U.S. Pat. No. 8,377,009, which claims benefit of priority to U.S. Provisional Application Nos. 60/982,643, filed Oct. 25, 2007, 60/978,619, filed Oct. 9, 2007, 60/944,700, filed Jun. 18, 2007 and 60/938,379, filed May 16, 2007. This application also claims benefit of priority to U.S. Provisional Application 61/231,587, filed Aug. 5, 2009, the disclosures of all of which are incorporated herein by reference for all purposes.

STATEMENT REGARDING FEDERALLY SPONSORED RESEARCH OR DEVELOPMENT

Not applicable.

BACKGROUND OF THE INVENTION

While the development of pharmaceutical drugs is important for continued improvement of therapeutic alternatives, pharmaceutical drug delivery methods can also play a crucial role in making drugs readily available to patient populations. The easier a therapeutic drug is to administer, the more interested a potential patient will be in the drug, thereby resulting in greater compliance with taking the drug. For example, transdermal patch delivery of nitroglycerin more than tripled the nitroglycerin market, because it made the benefits of this drug conveniently available to patients. Other drug delivery systems that have increased the availability of pharmaceutical drugs to patients are lozenges, topical creams and gels, oral cancer drugs, sustained release medicines, liposomes, and medical device applications, to name but a few.

Despite the advances made in other areas for novel drug delivery systems, the ophthalmic industry has lagged behind in improving the administration of drugs to users. Eye drops have been used for over 100 years for front of the eye diseases, and are still the most widely used method for administering drugs to the eye. In fact, over 95% of all ophthalmic drugs are delivered through a traditional eye drop bottle delivery system. But because drops administered from an eye drop bottle are relatively large, the instinctive blink that is provoked by the arrival of the large drop severely limits the amount of or proportion of fluid that actually contacts the target area on the eye. For example, less than 20% of a 50 μl drop may deliver effective treatment for a patient's eye, while the remainder is lost by drainage. The problem of drainage is further compounded by the natural limitations of the human eye to hold 7 μl to 12 μl before overflow occurs. This loss of expensive drug treatments is wasteful, and leads to uncertainty about the effectiveness of a treatment. For chronic users of certain ophthalmic drugs, this problem of overflow can also cause allergic reactions to the eyelid or in some cases staining of the skin surrounding the eye.

Another problem with overdosing the eye is systemic uptake of the drug as excess flows through the nasolacrimal duct to the back of the throat and potentially into the nasal cavity and stomach. For certain drugs such as beta blockers, undesirable systemic uptake can cause adverse respiratory or cardiac side effects. Thus, this traditional method of ophthalmic drug delivery, while affording a measure of simplicity for the user, has a number of problems, including waste and cost arising from errors in drug administration; over or under dosing arising from inexact administration of the drug; the need for preservatives in the drug to protect the efficacy of the drug once the dropper bottle is opened and exposed to air; eye irritation from exposure to preservatives required to maintain drug shelf life; loss of sterility or cross contamination of the drug; waste arising from discarding partially used bottles of the drug; accidental injury to the eye during administration; and no easy means of tracking compliance to the prescribed use of the drug. Still another disadvantage of conventional eye-droppers is that the amount of substance dispensed with an eye-dropper will depend on the amount of force the user applies to the eyedropper bottle, which presents an uncontrolled variable into the administration of a substance to the eye.

Ophthalmic drug delivery systems have been difficult to develop primarily because the eye has natural protective barriers, and is particularly sensitive to devices, implants and compounds that deliver drugs to the eye. Within the past decade, there have been a limited number of new device technologies developed that attempt to treat "front of the eye" disorders and diseases. These devices have been largely limited to reservoir based pump dropper systems that claim to maintain the sterility of the drug after the package has been opened. The commercial success of these systems is limited because they do not meet the critical challenge of making drug administration to the eye simple, precise and convenient. There is a market need for an effective multiple unit dose delivery system for ophthalmic drug administration, as evidenced by a study conducted by Beta Research Corporation, Syossett, N.Y., of a single unit dose administration using a first generation device to administer an ophthalmic drug to the front of the eye as an alternative to eye drops.

Another important consideration for the continued development of drug delivery systems is our aging population, and the increased care that people in this category need over time. For example, there are approximately 11.5 million people in nursing and assisted care centers in the U.S., and 59% need their medication administered by an assistant, taking up valuable resources, and depriving these people of their independence. As a result, there is a need for a comprehensive solution for certain patient populations, for example the elderly or those who are incapacitated, to self-administer pharmaceutical drugs in an easy and correct way. Some of the challenges facing institutional healthcare environments with respect to the administration of ophthalmic drugs to patients and residents include the time spent by caregivers administering eye drops to patients; potential liability as a result of accidental eye injuries which occur from faulty administration; increased cost due to waste; effective ophthalmic drug administration to uncooperative elderly and pediatric patients; cross contamination arising from using large institutional eye drop bottles; and the rising cost of drugs. Thus, an effective solution for addressing the shortcomings of using eye drop bottle delivery systems is needed.

SUMMARY OF THE INVENTION

The present disclosure is directed to delivery systems that administer single or multiple doses of one or more substances, for example a liquid, powder, or gel, to a user. The substance may be administered to a variety of locations, including but not limited to the front of the eye, the ear, the nose, the mouth, the skin, the lungs, the mucous membranes, or the rectum of the user. As used herein, the term "delivery system" is interchangeable with "delivery device" or "device." The delivery systems of the present disclosure can combine mechanically advantaged actuation and mechanically disadvantaged actuation with a dispensing mechanism to dispense a predetermined volume of substance to a particular destination with each administration, independent of the coordination of the user. For example, the combined actuation approach of the delivery systems may allow the force applied by the user to actuate the device such that it reaches a pre-defined minimum threshold level to dispense the substance contained in the unit dosage form. This feature ensures that sufficient force is applied to fully dispense the dose. Once the pre-defined minimum threshold level is reached, the system is mechanically advantaged such that administration requires minimal effort. This approach is designed to increase ease of administration of the disclosed delivery systems, which is particularly important for elderly or incapacitated users, who typically find it difficult to administer a substance, for example to administer eye drops, because of a physical infirmity such as arthritis, or other disabling conditions. Certain embodiments of the presently disclosed delivery systems are designed to allow a user to dispense a predetermined dosage of a substance accurately and easily. These delivery systems thus can overcome problems with aligning and dispensing from commercially available devices, for example eye dropper devices, particularly for users with physical limitations or poor motor skills.

In certain embodiments, the delivery systems disclosed herein offer one or more of the following advantages: cost savings (reduces waste from reducing errors in administration); improved efficacy from exact and consistent dosage administration; convenience and ease of use; improved patient compliance; improved safety; reduced or eliminated cross contamination; reduced or eliminated need for preservatives, thereby reducing the irritation and stinging the user would otherwise experience from the preservative; improved performance due to multi-unit dosing; improved ability to meet the needs of elderly, incapacitated, and pediatric patients; and the capability to package one or more substances in separate unit dose containers within the same device. In certain embodiments, these delivery systems also reduce potentially adverse side effects from the administration of certain drugs, by reducing the potential for systemic uptake and overflow out of the eye.

As used herein, the term "substance" includes but is not limited to one or more active-ingredient-containing substances wherein the active ingredient may be a biologic agents such as a protein, peptide, vaccine, or an active pharmaceutical ingredient ("API"), for example a pharmaceutical drug such as a prescription drug, generic drug, or over-the-counter pharmaceutical, neutraceutical or homeopathic product. The substance may be in an aqueous, gel, powder, solution, emulsion, crystals or suspension form. As used here, the term "substance" is interchangeable with the terms "drug," "drug product," "medication," "liquid," "biologic," "active ingredient" or "API." As used herein, an "active ingredient" or API is any component intended to furnish pharmacological activity or other direct effect in the diagnosis, cure, mitigation, treatment, or prevention of disease, or to affect the structure or any function of the body of humans or other animals. As used herein, the term "unit dosage form" is interchangeable with the terms "bottle," "vial," "unit-dose," "dosage form," "unit-dose vial," "blister," "dosage blister," "ampoule" or "container."

The present disclosure can be described in certain embodiments, as a drug delivery system that includes a housing configured to contain one or more crushable unit dosage forms; a user activation mechanism, effective when activated, to engage a drug delivery mechanism that includes a piston drivable into at least one dosage form contained in the housing, wherein the activation mechanism provides a mechanical advantage, a mechanical disadvantage or a combination of mechanical advantage and disadvantage to the activation mechanism; and a discharge port formed in or contiguous with the housing and configured to release the contents of a dosage form upon activation of the activation mechanism. By formed in or contiguous is meant that upon firing, a dosage form that is in the delivery position is positioned such that the piercing mechanism directs the contents of the dosage form out of the housing through the discharge port and into a delivery device designed for a particular use, such as an eye cup, for example.

In certain embodiments, the dosage forms are blisters, including a pierceable region and an internal piercing mechanism, wherein, the piercing mechanism includes an internal channel positioned to release the content of the blister through the piercing mechanism in a spray, stream, drops, or mist pattern and out the discharge port when the blister is crushed and the piercing mechanism pierces the pierceable region. Dosage forms can be packaged as individual blisters that are separated prior to loading into the devices, or they may be used as multiple loaded dosage forms. In certain embodiments the drug delivery system includes a mechanism to sequentially position a dosage form adjacent the dispensing channel and optionally to simultaneously advance a spent dosage form away from the dispensing channel.

The dosage forms can also be included in a cartridge that is replaceable in a drug delivery system. The housing is configured in such embodiments to accept a cartridge containing one or more blister dosage forms and to sequentially position the dosage forms in dispensing position when the dosage forms are provided on a disk, a ring or a strip, for example. In certain embodiments the devices include an indexing wheel connected to an indexing lever configured such that activating the indexing knob advances a unit dosage form into dispensing position, or they can include a winding take-up wheel/torsion spring in engagement with an indexing sprocket attachable to a strip of blister dosage forms.

It is an aspect of the disclosure that the activation mechanisms of the drug delivery systems, which can include a hinge, spring, cam, or motorized drive, can provide a mechanical disadvantage such that a pre-defined minimum threshold force must be applied to the activation mechanism in order to activate a drug delivery mechanism, and that the activation mechanisms can also provide a mechanical advantage such that, when activated the force driving the piston into the dosage form is greater than the simultaneous force applied to the activating mechanism. These two properties can also be combined in a single drug delivery device and operate sequentially. The mechanical properties, either mechanical advantage or disadvantage can be accomplished by use of a lever, cam or an inclined plane system. In certain embodiments a mechanical advantage or disadvantage is provided by an interaction of an angled face on an activation button and an angled face of a piston, or a mechanical advantage or disadvantage is provided by an interaction of an arcuate face on an activation button and an arcuate face on a piston. In certain embodiments the activation mechanism provides for a mechanical disadvantage during a first stage of activation until a minimum threshold force is exerted and a mechanical advantage during a second stage of activation during which a piston is driven into a dosage form.

It is an aspect of the disclosure that the dosage forms contain a substance that includes an active pharmaceutical ingredient or biologic. Because the dosage forms are single use, disposable dosage forms and are sterile prior to use, the substance can be preservative-free. In certain embodiments the dosage forms also include a head space of gas or air to ensure complete delivery of the dose. The substance is delivered or dispensed as a drop, droplet, stream or spray upon release from the unit dosage form.

The drug delivery systems of the disclosure can be configured to deliver the contents of a dosage form to a selected body part of a drug recipient, or a user, such as to an eye, nose, mouth, ear, or rectum of a recipient. In certain preferred embodiments, the devices are configured for delivery to the front of the eye, and such devices include an eyecup. The eye cups can include a detachable cap and such caps can also include storage capacity inside the cap for storage of dosage forms.

In certain embodiments the drug delivery systems can include a programmable microprocessor. The programmable microprocessor can be a Printed Circuit Board or an Application Specific Integrated Circuit coupled to a visual display interface and audible notification system, wherein the visual display interface is optionally a Liquid Crystal Display or Light Emitting Diode.

In still further embodiments, the disclosed drug delivery systems can be described as including a housing; a button on a surface of the housing and pivotable indexing lever that acts as a cover and an indexing lever from a closed position to a dispensing position; a firing mechanism comprising a piston connected to a link contained in the housing and in contact with the button through the link; a discharge port attached to the housing and in fluid communication with a unit dosage form dispensing position in the housing; and a feed mechanism for a blister strip contained in the housing, and comprising a feed wheel, an indexing wheel, and a take-up wheel, effective to sequentially move unit dosage forms contained on the blister strip into dispensing position in front of the discharge port by turning the indexing wheel; wherein when the dispensing button is in the raised position, depressing the button forces the piston into an unit dosage form in the dispensing position, thereby forcing the contents of the unit dosage form through the discharge port into the eye, and wherein the link provides a mechanical advantage to the piston. The link used in such systems can include an inclined plane cam or a lever.

Certain drug delivery systems are for delivery of dosage forms configured as blister strips including a plurality of internally pierced unit dosage forms. The delivery systems can include an indicator connected to the indexing wheel and visible from outside the housing, wherein the indicator comprises symbols to indicate the number of unused unit dosage forms on a blister strip. The symbols used in such a system can include numbers, letters, colors, or a combination of any thereof. The indexing mechanism can include a rotating lever, and optionally a rotating lever that also acts as a cover to the drug discharge area. Such devices can also include an indicator port adjacent to the discharge port and positioned to reveal dosage counter indicators on the delivery system when viewed from the exterior of the housing.

The precise and repeatable dosing features of the presently disclosed delivery systems overcome many of the disadvantages associated with known methods for dispensing substances to the eye of a user. Because the delivery systems disclosed can use an integral prepackaged unit dosage form that contains a precise dose, the delivery system makes the administration of the desired substance, for example an ophthalmic drug, simpler, faster, more convenient, more precise, safer, and less costly. To illustrate, in the ophthalmic industry some eye drop units of liquid are marketed as single-dose vials. These single-dose vials are manipulated and administered to the eye in the same manner as an eye drop bottle with all the same shortcomings. An important advantage of the presently disclosed delivery systems is that the user cannot refill the unit dose form once it has been dispensed. The one-time use nature of these unit dosage forms eliminates the reuse problem common with other marketed eye drop units, and the risks associated with improper reuse of unit doses.

An advantage of the presently disclosed delivery systems is that since gravity is not required for dispensing substance with these devices, as it is with eye-droppers, the delivery systems can be operated from a wide range of physical orientations, for example in an upright, horizontal, vertical, or downward position. This minimizes the need for users to adjust their physical position, for example by tilting back their head, during administration and reduces risks associated with loss of balance or neck injury.

Another advantage of the presently disclosed delivery systems is that they utilize unit dosage forms that maintain the sterility of the substance administered to the user until the moment of use and the dispensing path is only used one time and then discarded. Since the sterile substance is not exposed to air or the external environment due to the sealed containment within the unit dose form until actual usage, and the dispensing path is only used once, the loss of sterility is avoided.

Still another important advantage of the presently disclosed delivery systems is that they dispense precise amounts of the substance to a precise location, for example in the eye, thereby reducing the risk of over or under medication. Because of the precise unit dose form containing the drug, the more precise delivery system of the present disclosure also reduces waste from excessive or error prone delivery. This is important in the ophthalmic area, given the problems normally encountered with traditional eye drop bottles or other delivery systems for delivery of drugs to the eye. The precise amount of drug contained in the unit dose form blister allows the precise control of the amount of drug dispensed. Also, the internal or external piercer and nozzle provides controlled direction and form of the substance stream to the administration site. For example, when administered to the eye, the substance is directed into the eye in a precise location solving the problem of accurate dosing and increasing the effective amount of drug delivered to the eye.

In certain embodiments, the delivery systems are designed to dispense medication from a blister strip of unit dosage forms. Blister strips are well known in the art and may comprise a plurality of unit dosage forms in a single line connected on strip or in a disk for sequential administration. In certain embodiments, the delivery system can be supplied loaded with the blister strip, or the blister strip is preloaded into a disposable cartridge to be placed in the delivery system. The delivery system or cartridge can provide an indexing mechanism, e.g., an indexing wheel, button or lever, between the feed wheel and the take-up wheel with teeth or some other known mechanism for grasping the blister strip and advancing the strip when the indexing wheel is turned. Such indexing wheels often include a ratchet device effective to advance the blisters one at a time in sequence. Delivery systems can be indexed by a user to sequentially place a unit dosage form in the dispensing position, and remove the dosage form after it is dispensed. When all unit dosage forms have been used a new cartridge containing new dosage forms may then replace the cartridge. The delivery system or cartridge may contain a strip of unit dosage forms that are indexed to the dispensing position and wound on a take-up reel after dispensing such that the delivery system or cartridge contains new dosage forms and stores dispensed unit dosage forms within the device or cartridge.

In certain embodiments, the delivery systems disclosed herein are used to administer one or more therapeutically effective substances to a user, for example to the eye of a user. In some embodiments, the delivery system is used to administer one or more ophthalmic drugs. When more than one drug is to be administered, the delivery system can dispense multiple drugs that are combined in the delivery system as a mix or as a sequential series of specific drugs. The unit dose form can be used to contain multiple drugs that are dispensed together at the time of dispensing or multiple drugs can be combined in a sequence of unit dose forms in a strip or wheel to be sequentially dispensed by the user. This feature overcomes the problem of dispensing multiple drugs to the same user or a mix of drugs that require separate storage in the unit dose forms.

In other embodiments, the delivery system further comprises an eye cup that is adapted to conform to the shape of the user's facial area surrounding the eye socket of the user. In certain embodiments, the delivery system comprises an eye cup storage space for a separate and reusable eye cup, or for additional unit dosage cartridges. The delivery system further solves the problem of ease of use and accuracy by allowing the eye cup to function as an alignment feature to precisely locate and direct the drug drop, stream or spray into a precise location on the front of the eye.

To avoid contamination of the eye cup, some embodiments of the delivery systems include an eye cup cover that is removable or hinged or pivoted. To solve the problem of inadvertent dispensing, the delivery systems may have an interlock feature that prevents the delivery system from inadvertently dispensing when the cap is in place or closed.

In certain embodiments of the presently disclosed delivery systems, the indexing mechanisms allow a user to move a unit dosage form into the dispensing position between a discharge port and a piston or ram connected to the dispensing mechanism. Pressing the dispensing mechanism drives a plunger or piston into the unit dosage form in the dispensing position and drives the contents through an internal piercer nozzle, which is contained inside the unit dosage form. The internal piercer nozzle breaches the wall of the unit dosage form in a controlled manner and dispenses the contents of the unit dosage form through the piercer nozzle into the administration target. The piercer nozzle is fully contained within the dosage form and contains the nozzle within the sterile environment of the dosage form. The piercing nozzle can include a spray nozzle and other internal geometries such as flutes, ribs, spiral and angled dispensing paths to control the velocity and plume geometry of the emitted spray or stream of the substance.

Additionally, the disclosed delivery systems overcome the problem of inconsistent dose volume delivery arising as a result of variable force provided by the user during the dispensing process by controlling the force required to dispense the substance in the unit dosage form to a minimum force actuation threshold. It is an aspect of the disclosure that the interfacing surfaces of the dispensing button and the piston or ram that compresses the unit dosage form utilize a mechanical advantage or disadvantage or combination of both such that the force exerted by the user on the dispensing button, rocker or lever must reach a predetermined level, for example between a range of 2 to 8 pounds before the piston will advance and compress the unit dosage form. It is a further aspect of the disclosure that the interfacing linked surfaces of the dispensing button and the piston or ram utilize mechanical advantage in a manner that will increase the force applied by user to the piston or ram to achieve a uniform and consistent compression of the unit dosage form resulting in a uniform and repeatable dispense of the delivered dose volume and plume geometry. Mechanisms that may be used in the present disclosure include but are not limited to inclined plane, cams and lever mechanisms to provide mechanical advantage or disadvantage throughout the travel of the dispensing lever, paddle or button to control the feel and behavior of the force vs. position during dispensing.

The delivery systems may include a button, paddle, lever or rocker that is flush with the surface of the delivery system in storage mode and can be raised or tilted up on one end thereof into the ready position for administration. Indexing or tilting the rocker also places the firing mechanism into ready position with the button linked to a firing ram or piston adjacent to a dosage unit form. This allows simple indication that the delivery system is ready for dispensing and is positioned ready to be pressed down to dispense the drug.

In additional embodiments, the dispensing mechanism uses the button, paddle, rocker or charging lever to store energy in a spring. When the charging button, paddle, rocker or charging lever is pressed, the travel compresses a spring that is locked by the dispensing release. This spring is then released or triggered by a dispensing release button to fire the piston or ram to dispense the fluid.

In addition, space within the dosage unit form beyond the substance provides volume for air or gas to allow compressibility of the dosage form for crushing travel to allow an internal piercing nozzle to travel forward for piercing prior to dispensing the substance. This compressible space within the blister form allows travel of the piston plunger for piercing without creating high resistance to compressing the unit form during the initial travel of the piston for piercing.

The problem of disposal of the dispensed unit dose forms from the delivery system can be addressed in different ways in different embodiments. In some embodiments, the delivery system or removable cartridge is disposable and the delivery system or cartridge stores the spent blisters internally for disposal after the exhaustion of all of the filled unit dose blisters. In other embodiments that use a strip of unit dose blisters, the spent blisters are cut and expelled from the delivery system when indexed. This is accomplished by including a cutting mechanism that allows the dispensed blister to be cut-off from the strip and fall from the delivery system for disposal.

In addition, some circumstances of use would not allow the convenient cutting and disposal of each dispensed unit dose form blister every time the devise is indexed. A unique solution to this problem is the inclusion in some embodiments of a buffer storage capability that allows the delivery system to be indexed and dispensed several times without disposing of the dispensed unit dose form blisters. A separately actuated cutting mechanism allows several dispensed unit dose forms that are contained within the delivery system prior to disposal to be cut and expelled. After the delivery system is dispensed and indexed several times, the group of dispensed forms on the strip are cut and expelled as a group (plurality of spent dose forms on the strip) from the delivery system. This feature allows dispensing of several doses without expelling the dispensed forms (on the strip) and an ability to delay the disposal of the spent blisters until a later convenient time.

The disclosed delivery systems can also be actuated through the use of an electronically controlled, battery powered, electro-mechanical firing mechanism. The problem of tracking the number of doses used and remaining can be overcome by including a counting and display function in the electronic control that displays dose information to the user. In addition, an embodiment using electronic control of the dispensing electro-mechanical mechanism can include control of the positioning of the dispensing piston or ram such that partial travel may be controlled providing the ability to partially dispense the substance from the unit dose form in one step and then dispense the remainder of the substance in the second step. This feature provides capability for a multi-step dispensing for a single unit dose form.

Throughout this disclosure, unless the context dictates otherwise, the word "comprise" or variations such as "comprises" or "comprising" is understood to mean "includes, but is not limited to" such that other elements that are not explicitly mentioned may also be included. Further, unless the context dictates otherwise, use of the term "a" may mean a singular object or element, or it may mean a plurality, or one or more of such objects or elements. In addition, the use of "or" herein means "and/or" unless specifically stated otherwise. Also, terms such as "element" or "component" encompass both elements and components comprising one unit and elements or components that comprise more than one unit unless specifically stated otherwise.

It is to be understood that both the foregoing general description and the following detailed description are exemplary and explanatory only, and are not restrictive of the invention, as claimed. The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8 is an illustration of the indexing sprocket and indexing post

FIG. 12 is an illustration of a preferred embodiment with storage cap removed.

FIG. 13a and FIG. 13b are illustrations of a replaceable drug cartridge.

FIG. 24 is an illustration of the delivery system showing internal components and mechanism with the top half of the body removed.

FIG. 25a and FIG. 25b are illustrations of another embodiment of an ophthalmic delivery system with a built in drug form strip disposal capability. FIG. 17b shows the drug form strip disposal.

FIG. 35B is a section of the drawing in 35A.

FIGS. 36B and 36C are sections of drawing 36A in which FIG. 36C shows the device in the ready position, and FIG. 36B shows the device when fired.

DETAILED DESCRIPTION OF THE INVENTION

Figure 1:
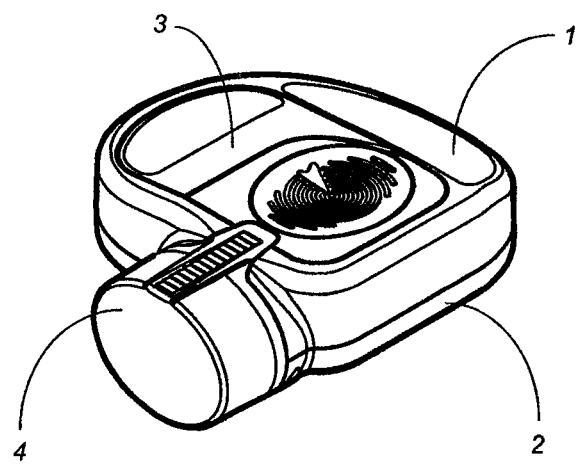
FIG. 1 is an illustration of a preferred embodiment of an ophthalmic multi-dose delivery system.

The present disclosure is directed to delivery systems able to dispense single or multiple doses of one or more substances, for example that contain an active ingredient (such as a pharmaceutical drug) or a biologic to a user. The delivery systems can be modified to dispense the substance via different routes of administration including but not limited to: oral, peroral, enteral, parenteral, pulmonary, rectal, dermal, otic, topical, nasal, vaginal, lingual, direct injection, intravenous, intraarterial, intracardial, intradermal, intramuscular, intraperitoneal, intracutaneous, intraocular, ophthalmic, intranasal, intrapleural, intrathecal, intratumor, intrauterine, orthotopic, transdermal, buccal, subcutaneous, or other routes of delivery. In other embodiments, the delivery systems can deliver a desired substance to the eye, ear, nose, mouth, skin, lungs, mucous membranes, or rectum of the user. Certain embodiments disclosed herein are to ophthalmic delivery systems for dispensing a predetermined substance or substances to the eye of a user. As used herein, the term "user" is interchangeable with the terms "subject" or "patient," and refers to a mammal, preferably a human, as well as to other animals, for example, cats, dogs, mice, cows, horses, pigs, and the like. The user can include, therefore a recipient of the drug dose that is not the person actuating the mechanism.

Other embodiments of the delivery systems disclosed herein incorporate an ergonomic design that makes the devices easy to operate, particularly for the elderly, and reduces the time needed for administering the predetermined substances. In certain embodiments, the delivery systems are portable hand-held devices that utilize disposable unit dosage forms containing the substance(s) to be administered to the user. Delivery systems for the ophthalmic delivery of drugs may further include an eyecup. The delivery systems can be configured either for self-administration or for use by a caregiver, such as medical and health care professionals, for example, in an institutional setting such as a hospital, clinic, nursing home, assisted living environment, physician's office, pediatric center and veterinary medical clinic or agricultural setting. In some embodiments, the delivery systems are used for ophthalmic drug delivery applications, such as for the treatment of dry eye, allergies, glaucoma, cataracts, macular degeneration or other chronic eye problems or diseases. Other embodiments of the delivery systems may be used for the administration of anti-infective agents such as antibiotics or bacteriostatic compounds, anti-inflammatory agents, or biologics. Still other embodiments of the delivery systems are directed to delivery of substances for intramuscular or subcutaneous injection, or alternatively delivery of substances to the eye, ear, nose, mouth, skin, lungs, mucous membranes, or rectum. Such embodiments may incorporate an interface appropriate for matching the administration route of the delivery system to the appropriate site of administration, for example by incorporating a needle, a nasal applicator, or an otic applicator into the delivery system.

One disadvantage of using eye drop bottles to dispense liquids to the eye is that often times too much liquid is administered to the eye, or the dispensed droplet misses the eye, resulting in waste of the substance, as well as potentially resulting in over or under dosing of the medication. For example, with a conventional eye-dropper, the smallest droplet of an aqueous drug solution that will free fall from the tip of the dropper is approximately 35 µl-50 µl of liquid due to the effect of surface tension between the liquid, the tip of the dropper, and the liquid remaining inside the tip. Considering the maximum volume of liquid that the eye can receive is 7 µl to 12 µl, a significant portion of the administered substance is wasted or systemically absorbed into the body. The presently disclosed delivery systems overcome these drawbacks by allowing for the administration of smaller and more precise volumes of liquid to, for example, the eye of a user. Preferably, the liquid dispensed by the delivery systems is discharged as a drop, spray or coherent stream of droplets, for example into the user's eye. Preferably, the plume geometry of the spray pattern distributes the substance across the surface of the eye in a manner that improves absorption and therapeutic results. In other embodiments, the liquid can be dispensed as a fine mist into the user's nose. Another advantage of the presently disclosed delivery systems is that the eyecup reduces the user's eye blink rate, which means the patient is less likely to blink during administration. In addition, the delivery systems disclosed herein preferably delivers the substance at a mass, velocity and plume geometry, which makes the user less likely to blink during administration and reduces the tear response improving residence time of the substance in the eye and absorption of the substance, thereby facilitating administration and efficacy of the substance for the user.

In certain embodiments of the present disclosure, the volume of the substance, for example droplets or particles, dispensed from the delivery systems to the eye is from about 7 µl to about 30 more preferably from about 8, 9, 10, 11, 12, 13, 14, 15, 16, 17, 18, 19, 20, 21, 22, 23, 24, 25, 26, 27, 28, 29 or about 30 µl. In other embodiments disclosed herein, small volumes of substance may be administered using the delivery devices disclosed herein, for example about 5 µl to about 500 µl, about 10 µl to about 400 µl about 15 µl to about 300 µl about 20 µl to about 250 µl about 50 µl to about 750 µl, and about 100 µl to about 1000 µl. In general, for the values provided herein, the term "about" indicates that a given number may vary by at least 5%, with variations of 10%, 15% or 20% being possible.

The volume and size of droplets or particles released by a delivery system can be adjusted to maximize the therapeutic benefit of the dispersed substance. The volume of substance dispensed depends on the volume and geometry of the unit dosage form, the piercer, the fill level, the degree to which the dosage form is compressed by the device and other variables in the construction of the delivery systems, as well as characteristics of the substance dispersed, which are well understood by those skilled in the art. These variables can be appropriately dimensioned to achieve dispersal of a desired volume or droplet size of liquid or particle size of substance to the user for example to provide greater coverage on the surface of the eye to improve absorption or reduce the tear response and the resulting wash out that typically occurs.

An advantage of the delivery system and unit dosage form designs set forth herein is that the sterility of the administered substance is maintained until the moment of use. Maintaining sterility until the moment of use minimizes or eliminates the need to use preservatives or bacteriostatic compounds in the substances administered, without risking contamination.

In certain embodiments, the substance dispensed from the delivery systems disclosed herein is an API, including but not limited to the following therapeutic compounds: anti-glaucoma/IOP (intra-ocular pressure) lowering compounds (e.g., β-adrenoceptor antagonists, such as carteolol, cetamolol, betaxolol, levobunolol, metipranolol, timolol; miotics, such as pilocarpine, carbachol, physostigmine; sympathomimetics, such as adrenaline, dipivefrine; carbonic anhydrase inhibitors, such as acetazolamide, dorzolamide; and prostaglandins, such as PGF-2 alpha); anti-microbial compounds, including anti-bacterials and anti-fungals, e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines; anti-viral compounds, e.g., acyclovir, cidofovir, idoxuridine, interferons; aldose reductase inhibitors, e.g., tolrestat;

anti-inflammatory and/or anti-allergy compounds, e.g., steroidal compounds such as betamethasone, clobetasone, dexamethasone, fluorometholone, hydrocortisone, prednisolone, and non-steroidal compounds such as antazoline, bromfenac, diclofenac, indomethacin, lodoxamide, saprofen, sodium cromoglycate; artificial tear/dry eye therapies, comfort drops, irrigation fluids, e.g., physiological saline, water, or oils; all optionally containing polymeric compounds such as acetylcysteine, hydroxyethylcellulose, hydroxymellose, hyaluronic acid, polyvinyl alcohol, polyacrylic acid derivatives; diagnostics, e.g., fluorescein, rose bengal; local anesthetics, e.g., amethocaine, lignocaine, oxbuprocaine, proxymetacaine; compounds that assist healing of corneal surface defects, e.g., cyclosporine, diclofenac, urogastrone and growth factors such as epidermal growth factor; mydriatics and cycloplegics, e.g., atropine, cyclopentolate, homatropine, hysocine, tropicamide; compounds for the treatment of pterygium, such as mitomycin C, collagenase inhibitors (e.g., batimastat); compounds for the treatment of macular degeneration and/or diabetic retinopathy and/or cataract prevention; and compounds for systemic effects following absorption into the bloodstream after ocular, intranasal, oral, or otic administration, e.g., chemical drugs, proteins and peptides such as pain medication for migraine or chronic pain management, vaccines, insulin, histamines, corticosteroids decongestants, and hormones.

In other embodiments, the substance is well-suited for intranasal delivery, including but not limited to FluMist (Mediimmune), Imitrex (Glaxo), Migranal (Xcel), Miacalcin (Novartis), Nascobal Gel (Nastech/Questcor), Nicotrol (Pfizer), Stadol NS (Bristol-Myers-Squibb), Stimate (Aventis Behringer), Synarel (Pfizer), Zomig (AstraZeneca), Apomorphine (Britannia Pharm), Apomorphine (Nastech), Emitasol (Questor), Fentanyl (West Pharm), FluINsure (ID Biomedical), Fortical (Unigene), Hypnostat (Questcor), Insulin (Bentley Lab), Interferons (Nastech), Ketamine (IDDS), Leuprolide (West), Migrastat (Questor), Morphine (West), Morphine Gluconate (Nastech), Nascobal Spray (Questcor), Somatropin (Nastech), Scopolamine, Amyl Nitrite, Peptide YY 3-36 (Nastech), PH948 (Pheriin), PH80 (Organon/ Pherin), Triptan (Nastech), and Vaccines (West). In still other embodiments, the substance is a vaccine, for example a vaccine to diphtheria, tetanus, acellular pertussis, Influenza, Herpes Simplex, Hepatitis A, Hepatitis B, Hepatitis C, Measles, Mumps, Rubella, Pneumoccal conjugate, Polio, Anthrax, Rabies, Typhoid, Yellow fever, Smallpox, Ebola, Hanta, Malaria, Rift Valley Fever, Encephilitus, Tuberculosis, SARS, and Attenuvax (Merck).

In still other embodiments, the drugs well-suited for intranasal delivery include but are not limited to alprazolam, chlorodiazepoxide, clonazepam, clorazepate, ciazepam, estazolam, flurazepam, flunitrazepam, halazepam, loprazolam, lorazepam, lormetazepam, midazolam, nitrazepam, oxazepam, prazepam, quazepam, temazepam, eszoplicone, indiplon/indiplone, zaleplon L-846, Quilor zopiclone, zolpidem tartrate, diphenhydramine, hydroxyzine, secobarbital, pentobarbital, tadalafil, vardenafil, sildenafil, alprostadil, caffeine, scopolomin, opiates (e.g., morphine, codeine, hydromorphone, hydrocodone, oxycodone, oxymorphone, desomorphine, diacetylmorphine, nicomorphine, dipropanoylmorphine, benzylmorphine, ethylmorphine, fentanyl, pethidine, methadone, tramadol, propoxyphene), lidocaine, epinephrine, human growth hormone ("HgH"), recombinant follicle stimulating hormone ("rFSH"), anticonvulsives (e.g., acetazolamide, carbamazepine, clonazepam, diazepam, divalproex, ethosuximide, lamotrignine acid, levetriacetam, oxcarbazepine, phenobarbital, phenyloin, pregabalin, primidone, remacemide, trimethadione, topiramate, vigabatrin, zonisamide), anti-emetics (e.g., acetylleucine monoethanolamine, alizapride, benzquinamide, bietanautine, bromopride, buclizine, chlorpromazine, clebopride, cyclizine, dimenhydrinate, dipheniodol, domperidone, granisetron, meclizine, methalltal, metoclopramide, metopimazine, nabilone, ondansteron, oxypendyl, pipamazine, piprinhydrinate, prochlorperazine, scopolamine, tetrahydrocannabinols, thiethylperazine, thioproperzaine, timethobenzamide, tropisetron), drugs for the treatment of Parkinson's Disease and Alzheimer's Disease (e.g., biperiden, bromocriptine, cabergoline, carbidopa, donezepil, 1-hydroxy-tacrine, galantamine, levodopa, lisuride, pergolide, pramipexole, quinpirole, ropinirole, rivastigmine, physostigimine, selegiline, tacrine, teruride), corticosteroids (e.g., dexamethasone, betamethasone, triamcinolone, triamcinolone acetonide, triamcinolone diacetate, triamcinolone hexacetonide, beclomethasone, dipropionate, beclomethasone dipropionate monohydrate, flumethasone pivalate, diflorasone diacetate, fluocinolone acetonide, fluorometholone, fluorometholone acetate, clobetasol propionate, desoximethasone, fluoxymesterone, fluprednisolone, hydrocortisone, hydrocortisone acetate, hydrocortisone butyrate, hydrocortisone sodium phosphate, hydrocortisone sodium succinate, hydrocortisone cypionate, hydrocortisone probutate, hydrocortisone valerate, cortisone acetate, paramethasone acetate, methylprednisolone, methylprednisolone acetate, methylprednisolone sodium succinate, prednisolone, prednisolone acetate, prednisolone sodium phosphate, prednisolone tebutate, clocortolone pivalate, flucinolone, dexamethasone 21-acetate, betamethasone 17-valerate, isoflupredone, 9-fluorocortisone, 6-hydroxydexamethasone, dichlorisone, meclorisone, flupredidene, doxibetasol, halopredone, halometasone, clobetasone, diflucortolone, isoflupredone acetate, fluorohydroxyandrostenedione, beclomethasone, flumethasone, diflorasone, fluocinolone, clobetasol, cortisone, paramethasone, clocortolone, prednisolone 21-hemisuccinate free acid, prednisolone metasulphobenzoate, prednisolone terbutate, and triamcinolone acetonide 21-palmitate), and drugs for the treatment of Multiple Sclerosis (e.g., interferon beta-1a, interferon beta-1b, glatiramer acetate, mitoxantrone, natalizumab). These drugs may also be administered using the other delivery system embodiments disclosed herein.

The active-ingredient-containing substances administered by the delivery systems disclosed herein may be the free acid or free base form of the active ingredient, or alternatively a salt, ester, pro-drug, or other more stable or more soluble form of the active ingredient. In addition, the delivery systems disclosed herein may be used to treat a patient with one or more active-ingredient-containing substances. The active-ingredient-containing substances are preferably formulated as aqueous solutions, gels, powders, solutions, crystals or suspensions. These formulations may optionally contain other formulation excipients, including but not limited to absorption enhancers or thickening agents such as gels, mucoadhesives and polymers, stabilizers, anti-oxidants, preservatives, and/or pH/tonicity adjusters.

The delivery systems disclosed herein are able to dispense single or multiple doses of one or more substances to a user by utilizing unit dosage forms. In certain embodiments, a unit dosage form contains a single-unit dose of a substance, a two-unit dose of one substance or two different substances, or a multi-unit dose of one or more substances, in one or more chambers of the unit dosage form. Alternatively, a unit dosage form may administer three or more substances from one or more chambers in a unit dosage form. During manufacture, the unit dosage forms can be singulated, i.e., individually broken apart and individually loaded into, for example, a unit dosage form cartridge or a delivery system. Alternatively, the unit dosage forms can be interconnected, for example through a strip, disk or connected webbing. The unit dosage forms can be manufactured as an array, which then may be manipulated into different forms such as a disk, strip, ring, or individually singulated for use in delivery systems or cartridges that can be preloaded and inserted into a delivery system. In other embodiments, the delivery systems, or the cartridge containing unit dosage forms, adhere to a numbering, color coding, icon system coding, or Braille system for assisting the user in administration of the unit dosage forms, and may also include a bar code or Radio Frequency Identification Device (RFID).

In general, the unit dosage forms as disclosed herein are single unit dose, sterile containers used to hold and dispense a wide range of substances to the eye, ear, nose, mouth, skin, lungs, mucous membranes, or rectum of a user. Ophthalmic applications include but are not limited to using the unit dosage forms to administer substances such as drug products, chemical drugs, or biologics to treat glaucoma, allergies, dry eye, macular degeneration. In other embodiments, the delivery systems may be used to administer ocular dilation, eye-flushing compounds, anti-infective agents or anti-inflammatory drugs. The delivery systems of the present disclosure may also be designed to administer intranasal drugs, including but are not limited to drug products, chemical drugs, or biologics for migraines, pain management, hormones, sleep dysfunction, erectile dysfunction, central nervous system disorders, seizures, emesis or allergies. In other embodiments, the delivery systems may be used to administer anti-infectives, anti-virals, vaccines, glucagon, or insulin. Otic drugs known to those in the art include but are not limited to anti-infective agents and anti-inflammatory drugs. It is also understood that additional drugs known to those of skill in the art, as well as drugs yet to be discovered, may be administered to users by utilizing the presently disclosed unit dosage forms and delivery systems.

Unit dosage forms utilized in the presently disclosed delivery systems may be small, ranging from about 0.5 cm to about 2 cm in diameter, or about 1 cm to about 1.5 cm in diameter. In certain embodiments, single-unit dose ophthalmic unit dosage forms range in size (interior volume) from 20 µl to 70 µl, while two-unit dose ophthalmic unit dosage forms range in size (interior volume) from 40 µl to 180 µl. In other embodiments, single-unit dose intra-nasal unit dosage forms range in size (interior volume) from 60 µl to 150 µl while two-unit dose intra-nasal unit dosage forms range in size (interior volume) from 100 µl to 400 µl. In still other embodiments, oral and otic unit dosage forms will have interior volume capacities that fall within ranges from 50 µl to 500 µl. It is understood that the volumes described in this paragraph are based on the volumes necessary to deliver an effective dose that is of an appropriate volume for the route of administration and type of substance being administered, and are primarily based on the treatment of human subjects. The optimal dosage of administered of a particular substance to a subject will be determined by methods known in the art and may vary depending on such factors as the subject's age, weight, height, sex, general medical/clinical condition, previous medical history, disease progression, formulation, concomitant therapies being administered, observed response of the subject, and the like. Unit dosage forms for delivery to agricultural or domestic animals may also vary in size and volume, as understood by one of skill in the art.

In some embodiments, the unit dosage forms contain a substance, for example an active-ingredient-containing substance, or a combination of both a substance and sterile air or other inert gas or vacuum depending upon the type of substance packaged in the unit dosage form, concentration of the substance, active ingredient bioavailability requirements, and the unit dosage form design utilized. In certain embodiments, the delivered dose efficiency of a unit dosage form ranges from about 50% to about 90%, depending upon the unit dosage form design utilized, delivery system and fill volume ratio. In other embodiments, the delivered dose efficiency of a unit dosage form ranges from greater than about 50%, about 55%, about 60%, about 65%, about 70%, about 75%, about 80%, about 85%, about 90%, about 95%, about 98%, or about 99%, depending upon the unit dosage form design utilized, delivery system and fill volume ratio. The delivered dose efficiency is the ratio of the volume of substance actually delivered to the destination and the volume of substance contained in the unit dosage form.

It is an aspect of the present disclosure that the unit dosage forms include one or more internal chambers, which contains a substance to be administered, which is in fluid communication with, or is adjacent to, a pierceable section of wall of the unit dosage form. This wall may be an interior or exterior wall. Various unit dosage form designs and piercing embodiments are disclosed herein in which the section of the exterior wall of the unit dosage form may be pierced or opened by the appropriate device to release the substance in the unit dosage form. In certain embodiments, the chamber of the unit dosage form includes an internal piercer (e.g., see U.S. Pat. Nos. 5,411,175 and 7,669,597, and U.S. application Ser. Nos. 11/114,251, 11/971,471, and 12/694,849, each of which is incorporated herein by reference). In certain embodiments, a piercer may move toward and pierce the pierceable section of the chamber to allow dispersion of the substance, or the pierceable section may move toward and be pierced by the piercer.

The piercers may be made from USP Class VI materials, such as plastics, ceramics, plastic laminates, plastic metal laminates, or metal, and may be constructed such that applying the appropriate pressure, for example by the delivery system firing mechanism compressing the unit dosage form, causes the piercer to breach the pierceable section of the unit dosage form, thereby releasing the contents of the unit dosage form in a controlled manner. The internal piercer may be located in the same chamber as the substance, adjacent to the chamber, or external to the chamber. The unit dosage form can contain more than one internal piercer, and/or each piercer in a unit dosage form may contain one or more points that contact the pierceable section. For example, the unit dosage form may be designed such that the pierceable section is pierced by more than one piercer, or a piercer with more than one piercing point. Multiple piercing points may be used to increase the delivery rate of the substance in the unit dosage form. The piercer may be manufactured as an integral part of the unit dosage form, or independently of the unit dosage form. In certain embodiments, the substance in the chamber of the unit dosage form is sterile, and the sterility is maintained until the moment of administration. In some embodiments the piercer contains a channel through which the medication flows when dispensed. In other embodiments the piercer is open or closed at the end distal to the pierceable section.

The unit dosage forms disclosed herein may be designed to "dispense" under force compressing the unit dosage form from the rear. The force required to effectively fire a unit dosage form exerted by the piston or ram is preferably about 4 to 20 pounds, although this is balanced with other design requirements associated with ensuring unit dosage form integrity, shelf life, vapor pressure performance, and the unit dosage form manufacturing process limitations.

In certain embodiments, the unit dosage form stream or spray patterns and dispensed dose volume are consistent from unit dosage form to unit dosage form. For ophthalmic delivery, the substance may be delivered across the anterior surface of the eye to improve coverage and absorption. In some embodiments, the substance is driven out of the unit dosage form with sufficient linear energy to overcome the effects of gravity, e.g., the user is able to consistently deliver the substance into the eye reliably and safely when the user's head and eye orientation is perpendicular to the force/direction of gravity. Linear distance to be traversed by the substance from the unit dosage form to the surface of the eye is typically between about 10 mm and 35 mm. The primary design considerations of unit dosage forms and delivery systems disclosed herein are consistency of the delivered dose to the targeted destination in the eye, ear, nose, mouth, skin, lungs, mucous membranes, or rectum; droplet size, and force level that is comfortable, safe and efficacious for the user; as well as delivery precision to the targeted destination. Examples of such delivery systems are described in pending U.S. application Ser. No. 11/971,471, which is incorporated by reference herein in its entirety.

The delivery systems and unit dosage forms of the present disclosure may incorporate one of the following mechanisms for piercing the unit dosage form to administer the one or more predetermined substances, for example by producing a drop or coherent stream of droplets or spray plume for delivery of the substance in the unit dosage form to the eye.

In certain embodiments, the internal piercer includes an internal channel (the delivery channel) through which the substance flows as the unit dosage form is compressed and pierced. The inside diameter of the delivery channel can range from about 0.008 inches to about 0.030 inches, but may also be about 0.010 or 0.020 inches. The internal diameter, shape, or surface texture of the delivery channel, whether in, near, and/or at the exit point, may contain a nozzle or may be varied to form the optimum droplet size and spray plume geometry of the substance as it exits the unit dosage form, as well as control the velocity, pressure, pattern, distribution, and aim of the released substance. Thus, the nozzle system and the piercer may be integrated into a single unit. The nozzle system can also be designed to determine the mixing of the substance as it is released. Internally pierced unit dosage forms may be single-dose, two-dose, or multiple-dose units.

Internally pierced unit dosage forms may be produced during the manufacturing process in a linear array and then cut into strips, disks or other suitable shapes containing multiple unit dosage forms or singulated into individual unit dosage forms. In certain embodiments, a strip of unit dosage forms is inserted into the delivery systems disclosed herein.

The unit dosage form manufacturing process may utilize both blister stock and lid stock as the primary material to form the blister. The blister stock material may be flexible but also capable of being molded using a combination of heat and pressure, can be crushed with a pre-determined force, creates a barrier protecting the drug substance from contamination, withstands radiation, and has desirable chemical properties (e.g., does not react adversely with the substance to be administered). Preferably the lid stock material may be puncturable at a limited distance, does not form flaps, is capable of splitting, creates a seal with the piercer, minimizes the generation of particulates, creates a barrier protecting the drug substance from contamination, withstands radiation, has desirable chemical properties (e.g., does not react adversely with the substance to be administered), and can be printed on. The lid stock or blister stock may consist of plastics, metals or other similar materials individually or combined together to form a multi-layered laminate.

Unit dosage forms of the present disclosure may be produced during the manufacturing process in an array with a connective material between each unit dosage form. In other embodiments, the connective material is used to form the unit dosage forms into a shape, for example a strip, disk, circle or individually singulated for insertion into a delivery system or cartridge. As used herein, a "cartridge" is container that can be inserted into a delivery system and capable of holding two or more unit dosage forms, which may be interconnected, or alternatively associated with, each other. The cartridge may be a disk-shaped enclosed container designed to hold a specific type of unit dosage form. In certain embodiments, the cartridge may serve one or more of the following purposes: (a) as a tamper-proof packaging container to protect cartridges during storage and transport; (b) to provide surfaces for labeling (manufacturer, type of substance, bar coding, expiry date, and prescription usage instructions); (c) to contain a gear or ratchet interface to the indexing mechanism in the delivery system allowing the unit dosage form cartridge to be indexed; (d) to contain at least one component of a security key which limits the installation and operation of a cartridge holder to authorized delivery systems and insures that cartridges are correctly loaded into the delivery system; and (e) to contain the unit dosage form numbering, color coding, or Braille system for assisting the user in compliance tracking, as well as a preferable mounting location for a Radio Frequency Identification Device (RFID).

In some embodiments, delivery systems and cartridges are constructed of polystyrene, or alternative types of approved medical grade plastics such as polypropylene, ABS, ABS/PC, PC/PTFE, Nylon 6, and polycarbonate. Delivery systems and cartridges may be of any size to accommodate the predetermined number of unit dosage forms, for example a delivery system or cartridge may be configured, in certain embodiments, to contain from 8 to 180 single-unit dose, two-unit dose, or multiple-unit dose unit dosage forms. In alternative embodiments, a delivery system or cartridge can be of different shapes such as rectangular, square, cylindrical, circular, oval or pyramidal, to accommodate alternate designs.

In other embodiments, a supply of unit dosage forms, such as a unit dosage form strip, loaded into a delivery system or cartridge contains one single type of substance in each unit dosage form. Alternatively, the unit dosage forms may contain two or more different substances in a pre-defined order, for example to administer two or more active-ingredient-containing substances, or alternatively two or more dosage levels of the same substance.

In still other embodiments, the delivery system or cartridge is labeled to identify the substance, and may also include a bar code and expiry date information in a manner that is easy for the user to read. The delivery system or cartridge may also use a color-coding scheme to provide a visual color reference to the user to enable them to determine the type of substance contained within the device.

In certain embodiments, an eye cup is incorporated into the delivery systems disclosed herein. The eye cup serves to position the delivery system in the correct orientation and distance from the eye. It may also facilitate opening the eyelid and holding the eyelid in the correct position during administration. The eye cup may be made from USP Class VI approved materials. The eye cup, for example, is made of soft, pliable plastic (or rubber) constructed of polyethylene, polypropylene, silicone or other medical grade materials that can be replaced by the user. In some embodiments, the eye cup material is transparent to enable a caregiver who may be aiding in the administration procedure to visually confirm the eyelid is open at the time the substance is dispensed.

In other embodiments, a cover or cap that is either removable or on a pivot or hinge covers the eye cup and substance dispensing aperture in the body of the delivery system to prevent contamination of the delivery system, the substance pathway, unit dosage forms, or accumulation of foreign matter in the delivery system or eye cup. In certain embodiments, selected components substance delivery path, and eye cup may use an antimicrobial coatings such as MICROBAN® to reduce the possibility of contamination. In still other embodiments, a cover or cap may be used in other delivery systems disclosed herein for the same purpose of facilitating administration of the predetermined substances, as well as maintaining sterile conditions during administration.

The eye cup may be replaced with other attachments, for example a nasal or otic applicator for alternative routes of administration. Delivery systems that will be used by a caregiver in an institutional care environment such as a hospital or nursing home across a wide range of users preferably incorporate individually loaded unit dosage forms with the desired substance and, for example, a sterile eyecup, nasal applicator or otic applicator for each administration. When a nasal or otic applicator is used, it is appropriately sized for insertion into the nose or ear. In embodiments intended for personal use, these interfaces can be reusable as there is limited concern for contamination. In embodiments intended for institutional application, however, the interface may be integrated with the unit dosage form and designed for a single use and then discarded, thereby minimizing the risk of cross-contamination between users.

The delivery system platform described by the present disclosure, termed VersiDoser™ Delivery System ("VDS") by the inventors, provides a platform technology that can be adapted for a variety of therapeutic delivery applications for ophthalmic drugs. The present disclosure generally categorizes the delivery systems disclosed herein as personal delivery systems or institutional delivery systems. It is important to note that any embodiment of a delivery system disclosed herein may be readily adapted to administer a substance from any type of unit dosage form disclosed herein by one of skilled in the art. Thus, the delivery system and unit dosage form combination chosen for administering a particular substance to a specific type of user using one of the disclosed routes (e.g., oral, peroral, enteral, parenteral, pulmonary, rectal, dermal, otic, topical, nasal, vaginal, lingual, direct injection, intravenous, intraarterial, intracardial, intradermal, intramuscular, intraperitoneal, intracutaneous, intraocular, ophthalmic, intranasal, intrapleural, intrathecal, intratumor, intrauterine, orthotopic, transdermal, buccal, subcutaneous) will depend upon factors such as the route of administration, physical properties of the substance to be administered (e.g., density, viscosity, surface tension), delivered dose volume, number of doses, and spray plume requirements.

Delivery systems of the present disclosure dispense the substance by compressing the unit dosage form, for example by piston action of the plunger in the delivery system, or by positive displacement of the substance in the chamber containing the substance. In certain embodiments, the compressive force of the firing mechanism of the delivery system is sufficient to cause the piercer to pierce the pierceable surface, as well as to disperse at least a portion of the substance from the chamber.

One of the advantages of the delivery systems disclosed herein is that they can administer more than one drug-containing substance or more than one drug to a user either simultaneously or sequentially. With respect to the delivery systems, two or more drugs may be combined together in a chamber of an unit dosage form immediately prior to administration, and subsequently administered to the patient, or alternatively the two or more drugs may be in separate chambers in the same unit dosage form until the moment of administration, at which time they are sequentially or jointly released from the same unit dosage form to the patient. For example, a first chamber in a unit dosage form contains a lyophilized drug or a drug in dry powder form, and a second chamber contains a liquid diluents, as disclosed, for example, in U.S. Pat. No. 7,669,597, incorporated herein by reference. The unit dosage form can be designed such that an area connecting the two chambers (e.g., a pierceable section) is breached (e.g., by a piercer) or through controlled delamination of laminate used to produce the unit dosage form, and the materials in the two chambers combine to, for example, reconstitute or suspend the pharmaceutically active drug in an aqueous formulation. The reconstitution or suspension of the two materials can be facilitated by, for example, by a static mixer contained within the unit dosage from in the dispensing channel After the liquid aqueous solution is formed, the drug is released from the unit dosage form, for example by the mechanisms disclosed herein, and administered to the user. In another embodiment, the two or more drugs are present each in their own respective adjacent chambers in sequence and the user administrates the first drug and then either immediately or after a therapeutically appropriate length of time administers the second drug followed by any additional drugs required in the sequence.

These embodiments can be used to administer as many different substances as are needed to the patient, as well as allowing a medical profession to tailor the therapeutic administration of selected substances to maximize their therapeutic benefits for the user. For example, a delivery system may be configured with a multi-dose blister strip that specifically provides the full regimen (prescription) of all ophthalmic drugs needed by a patient for the first several days to week after eye surgery. This includes prescription regimens that require a combination of different drugs that must be administered in a certain sequence at set times.

Alternatively, a delivery system can be configured with an electro-mechanical dispensing mechanism consisting of an electrically actuated piston, cam or screw drive. This configuration would preferably utilize a programmable microprocessor computer device such as a Printed Circuit Board (PCB) or an Application Specific Integrated Circuit (ASIC) combined with visual display to provide advanced control, notification and event logging capabilities in the delivery system. The delivery system can be programmed to remind the patient of the appropriate time to administer the next dose of drug, how many doses remain, automatic refill and reorder of a prescription and to alert the user when the delivery system should be replaced. This capability will greatly reduce the confusion many patients have over the complicated protocols involved with the post-operative or chronic care, and will result in better patient compliance and therapeutic treatment. The delivery system can also be designed to incorporate a number of safety features, for example a delay mechanism can be included in the delivery system to prevent the inadvertent delivery of an extra dose to the user. Another safety feature for the personal use delivery system is a child safety lock to prevent accidental discharge of the delivery system by a child. This delivery system also allows more patients to manage their own post-operative or chronic care, rather than requiring a caregiver to do so.

Certain delivery systems of the present disclosure are designed for repeated use by a single user and for self-administration. These delivery systems are referred to herein as personal delivery systems. In some embodiments, the delivery system design ergonomics of a personal delivery system allow the delivery system to be operable with either hand or both hands by a user. In addition, the operating components of the delivery system may be of sufficient size that they can be manipulated by an elderly or physically handicapped person with limited dexterity in their hands. This is accomplished by oversize controls and by operating actions that emphasize the use of gross motor skills over fine motor skills for most of the operating actions. In certain embodiments, surface treatment of the delivery system ensures the delivery system does not easily slip out of the hand during operation.

Certain embodiments of the delivery systems described herein include an absorbent strip which is used to absorb liquid from the dispense site that might otherwise contaminate subsequent doses. This is accomplished by overlaying a thin absorbent strip on the external pierceable region of the blister laminate with holes located at the piercing site. The holes allow the internal piercing mechanism to pierce and deliver drug without being impeded by the absorbent strip. Any fluid left on the internal piercing mechanism after the release of the blister fluid will wick to the absorbent strip which will contain the fluid and prevent uncontrolled entry of blister fluid into the device.

Certain embodiments of the delivery system described herein include a strip which is used to control when and how the pierceable region is pierced by the internal piercing mechanism. Controlling the pierce is accomplished by overlaying the external pierce site with a sheet of thin material with a hole, star, square or some other hole at the pierce site. The hole allows the piercing mechanism to puncture through the pierceable region without interruption by the puncture control strip but allows for additional control of the puncture site since the pierce control strip can have a different hole geometry than the dispensing port on the device housing.

Certain Embodiments of the delivery system described herein includes a dose counter which can keep track of doses remaining, doses used or any other dose count related number. The dose count can use any combination of numbering, icons or color codes. One embodiment of the dose counter may use a flexible sheet which is advanced by the takeup reel where the new dose count is shown, through a hole or transparent portion of the housing, due to the rotation of the takeup wheel. Another embodiment of the dose counter may use the unit dose strip, disk or other multiple dosage form configuration as the surface on which the dose count is indicated and is displayed through a hole or transparent portion of the housing. Another embodiment of the dose counter may use a cylinder or polygon which rotates to display the dose count. This embodiment may use more than one cylinder or polygon to display multiple dose counts and may be interconnected so that the dose count wheels can display dose counts on the order of magnitude of 10, 100 and 1000. The dose counter cylinder or polygon in this embodiment may be driven off of the takeup reel, sprocket, dispense button, index button or the movement of the dosage forms. Another embodiment of the dose counter may count the doses using a printed circuit board or integrated circuit and displayed on a digital readout. Doses can be counted via a switch which sends a signal to a printed circuit board or integrated circuit.

Certain embodiments of the delivery system described herein include a compressed air or fluid reservoir which is used to drive the plunger into the dosage form. This embodiment can include a regulator to ensure consistent operation as the reservoir pressure is reduced. A compressed air or fluid reservoir allows for a much lower dispense activation force for the operator which is advantageous in instances where multiple doses are administered in a short period of time. A compressed air or fluid driven dispense is more consistent since operator input is limited to a trigger of a release of pressure rather than providing the force to drive the plunger into the dosage form.

Certain embodiments of the delivery system described herein include a compressed spring which is used to drive the plunger into the dosage form. In this embodiment the spring, which is compressed prior to dispense by the user, provides a more consistent dispense since operator input is limited to a trigger of a release of stored energy rather than providing the force to drive the plunger into the dosage form.

Certain embodiments of personal delivery systems described herein include a button, lever or button mechanism on the top surface of the delivery system to actuate the dispense of the substance. The button typically lies flat against the top of the delivery system in a storage position and one end of the button is tilted upward, away from the device surface in the ready position. The button can impinge on a fulcrum device near the center thereof so that pressing on the end of the button furthest from the delivery outlet moves that end down, tilting the dispensing end up, or the button can be hinged on the end with the firing end pulled or pushed in an upward direction into the firing position. In the ready position, an indexing device can be used to advance a dosage blister or unit dosage form to a position adjacent a piston, ready for dispensing. In the ready position, depressing the button causes the piston to compress the dosage form and dispense the substance contained therein. It is a further aspect of the disclosed delivery systems that the dispensing mechanism provides a mechanical advantage to the user, such that the piston applies a greater force against the dosage form than the force applied to the button. In this way, users with less strength in their hands or fingers are able to self-administer the medication, and furthermore, it is easier for a weaker user to apply sufficient force to crush the dosage form with sufficient force to produce the desired spray pattern geometry of the dosage. In some embodiments of the delivery system, the interface surfaces between the dispensing button and the piston use a combination of mechanical disadvantage and mechanical advantage to achieve a minimum actuation threshold force that must be applied by the user before the device will actuate. This feature ensures that a consistent force is applied to compress the unit dosage form resulting in a delivered dose and spray plume geometry that is consistent and independent of the influence of the user.

Figure 2:
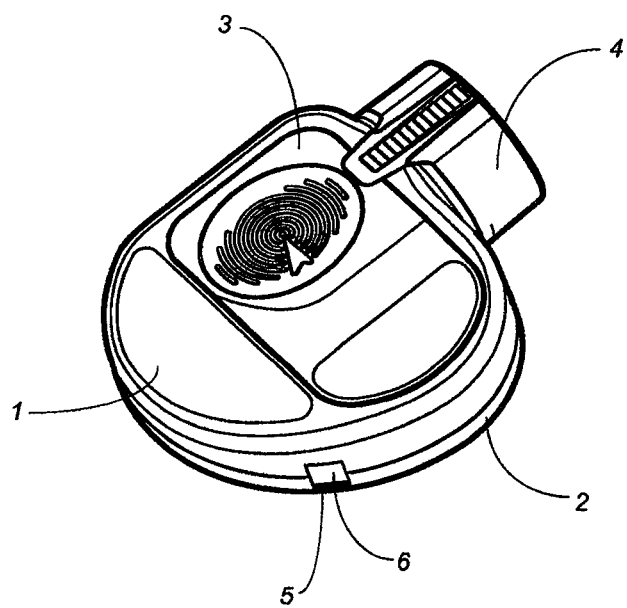
FIG. 2 is an illustration of a preferred embodiment multi-dose delivery system showing the dose window.
Figure 3:
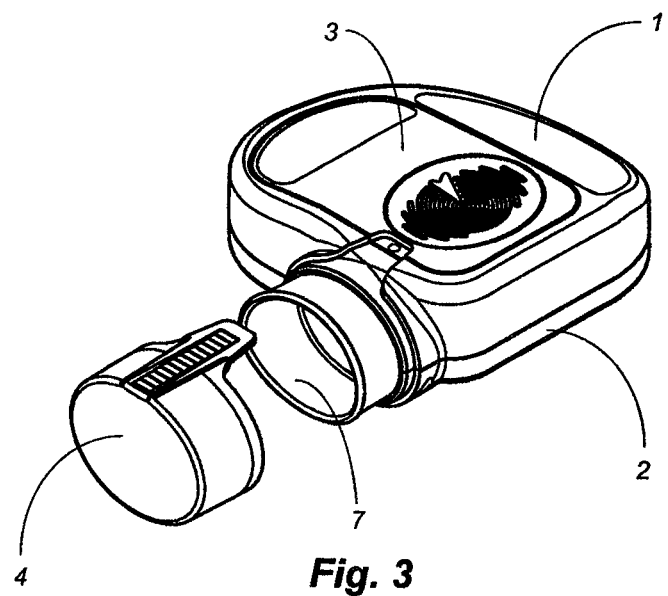
FIG. 3 is an illustration of a preferred embodiment multi-dose delivery system showing the eyecup and storage cap removed

In one embodiment of the delivery system, the unit is a disposable ophthalmic drug delivery device and contains a factory loaded unit dosage form strip containing the substance for dispensing. Referring to the drawings, and specifically to FIG. 1 and FIG. 2, a delivery system is shown in the storage configuration. This embodiment of the invention is a Button actuated self indexing ophthalmic delivery system and includes an Upper Housing 1 and Lower Housing 2, a pivoting Dispensing Button 3 and a Storage Cap 4. The Unit Dose Blister Strip consists of multiple unit dosage forms, each containing an internal piercer as disclosed in patent disclosure U.S. application Ser. Nos. 11/114,251, 11/971,471, and 12/694,849, and U.S. Pat. No. 7,669,597, each of which is incorporated herein in its entirety by reference for all purposes. The delivery system as shown in FIG. 1 is in storage mode and includes the removable protective Storage Cap 5 shown in place. The Dispensing Button 3 is held in the closed position by the Storage Cap 5 and is locked in this position by retention of the end of the Dispensing Button 3 by the snap-on Storage Cap 5 by disposing the Dispensing Button 3 to fit under the tab of the snap-on Storage Cap 5 as shown in FIG. 2. FIG. 3 shows the delivery system with the Storage Cap 5 removed and the Eyecup 6 and Dispensing Button 3 is illustrated.

Figure 4:
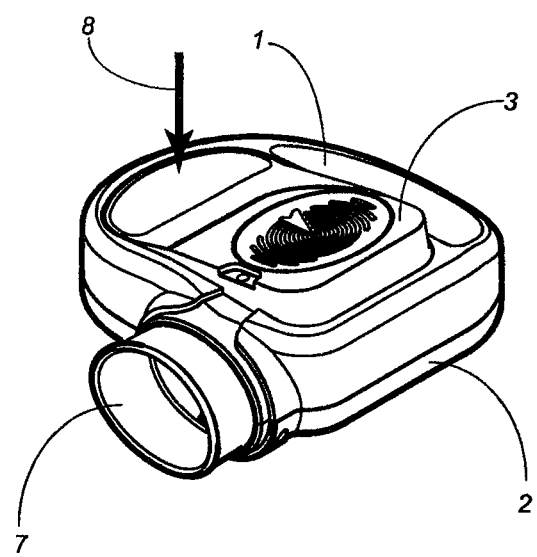
FIG. 4 is an illustration showing a preferred embodiment with the dispensing button in the ready position
Figure 5:
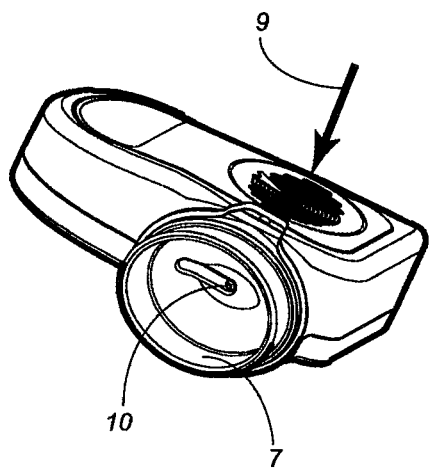
FIG. 5 is an illustration of a preferred embodiment multi-dose delivery system showing the eyecup and discharge port

This embodiment of the delivery system is also shown in FIG. 2 where a dose Counter Window 5 is visible. The dose Counter Window 5 allows a number ribbon Indexing Scroll 6 to pass by the dose Counter Window 5 internally and is synchronized with the dispensing of the unit such that an indication of the number of doses remaining is provided. When the Storage Cap 4 is removed, the Dispensing Button 3 is free to be pivoted and raised into the ready position as shown in FIG. 4. and the Eyecup 7 is exposed. The ready position is achieved by pressing on the Dispensing Button 3 as shown by arrow 8 and allowing the Dispensing Button 3 to pivot and tip up. The front oval portion of the delivery system includes an Eyecup 7 as shown in FIG. 5. and is placed to the eye to align and position the delivery system for dispensing the drug into the eye by pressing the Dispensing Button 3 as shown by arrow 9. The drug is dispensed from the discharge Port 10 as shown in FIG. 5 in the center back wall of the Eyecup 7. In this embodiment of the delivery system, a factory installed strip of unit dosage forms as described previously is coiled and wound internally and is advanced under spring force such that each time the Dispensing Button 3 is pivoted up into the dispensing position, the Unit Dose Blister Strip is indexed and automatically advances the Dose Blister into the next dispensing position.

Figure 6:
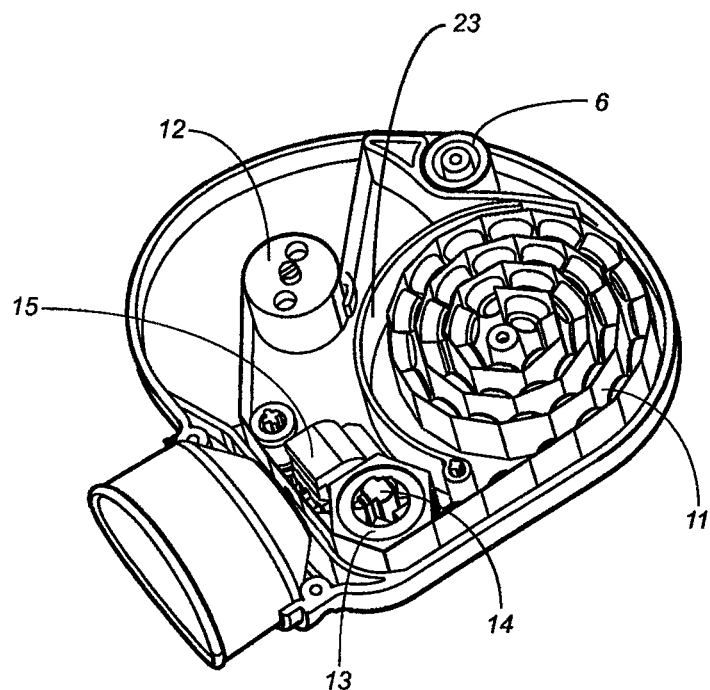
FIG. 6 is an illustration of the internal components of a multi-dose delivery system FIG. 7a and FIG. 7b is a cross section showing the Dispensing Button and Piston function with interfacing surfaces capable of providing mechanical disadvantage and mechanical advantage that can be adjusted by modifying the corresponding sloped surfaces control actuation force and compression force.

FIG. 6 shows the delivery system with the Upper Housing 1 and Dispensing Button 3 removed and internal components visible. FIG. 6 shows the coiled Unit Dose Blister Strip 11, a Take-up Wheel/Torsion Spring 12, Indexing Sprocket 13 and Indexing Post 14, Piston/Spring 15.

The portion of the mechanism for dispensing the drug includes a sliding dispensing Piston/Spring 15 also shown in FIG. 6. In addition, the dispensing mechanism is shown in cross section in FIG. 7*a* and FIG. 7*b*. Dispensing is accomplished by pivoting the Dispensing Button 3 to the dispense position by pressing the Button behind the pivot point as in FIG. 4 arrow 8. Spring force pushes the Piston/Spring 15 back and thereby retracts the Piston 15 maintaining contact with the cam surface 16 of the Dispensing Button 3. At this point, the Indexing Post 14 releases the Indexing Sprocket 13 to rotate to the next position and the Take-up Wheel/Torsion Spring 12 pulls the Unit Dose Blister Strip 11 forward to the next dispense position and aligns a Unit Dose Blister under the Eyecup discharge Port 10.

The cross sections FIG. 7*a* and FIG. 7*b* show the interaction of the Dispensing Button 3 and the sliding Piston/Spring 15. The return Spring in the Piston/Spring pushes it into a retracted position. Piston/Spring 15 has a cam surface 17 that interacts with the cam surface 16 on the Dispensing Button 3 as shown. When the Dispensing Button 3 is pressed as shown by FIG. 7*a* and FIG. 7*b* arrow 18, the Dispensing Button 3 moves down and the cam surface 16 presses against the cam surface 17 of Piston/Spring 15 thereby imposing a force in the direction of arrow 19. This moves the sliding Piston against the Unit Dose Blister contained in the Unit Dose Blister Strip 11 crushing the blister and thereby dispensing the dose through the discharge Port 10 of the Eyecup 7 towards the eye positioned in front of the Eyecup 7. In this embodiment, the relative angle and shape of the cam surfaces 16 and 17 on the Dispensing Button 3 and Piston/Spring 15 provide a mechanical advantage or disadvantage to control the force required to press the Dispensing Button 3 and create sufficient force to crush the Unit Dose Blister and produce the desired spray plume geometry. After the unit dosage form has been dispensed, the Dispensing Button 3 comes to rest in the storage position as shown in FIG. 7*b* and FIG. 3. After dispensing the drug, the Dispensing Button 3 remains in place and the Storage Cap 4 is replaced and thereby holds the Dispensing Button 3 in the storage position as shown in FIG. 1 and FIG. 2. If additional dispensing is needed prior to storage, the Dispensing Button 3 is returned to the dispense position by pressing the Button behind the pivot point as in FIG. 4 arrow 8 to tip the Dispensing Button 3 up allowing it to return to the dispensing position. Spring force retracts the Piston/Spring 15 maintaining contact with the cam surface 16 of the Dispensing Button 3. At this point, the Indexing Post 14 releases the Indexing Sprocket 13 to rotate to the next position and the Take-up Wheel/torsion spring 12 pulls the Unit Dose Blister Strip 11 forward to the next dispense position and aligns a fresh Unit Dose Blister under the drug discharge Port 10.

Referring to FIG. 6, a coiled Unit Dose Blister Strip 11 is attached to a winding Take-up Wheel/Torsion Spring 12 and is in engagement with the Indexing Sprocket 13 through tension on the Unit Dose Blister Strip 11 such that controlled rotation of the Indexing Sprocket 13 advances the Unit Dose Blister Strip 11 to align the next Unit Dose Blister for dispensing from the Eyecup 7. The Unit Dose Blister Strip 11 is engaged with recesses in the Indexing Sprocket 13 and maintains rotational alignment with the Unit Dose Blisters and allows the Indexing Sprocket 13 to be positionally synchronized with the Indexing Sprocket 13 rotational position. The Take-up Wheel/Torsion Spring 12 is pre-wound at factory assembly and supplies a constant force on the Unit Dose Blister Strip 11 to wind onto the Take-up Wheel/Torsion Spring 12. When the Indexing Sprocket 13 is released and allowed to rotate, the Unit Dose Blister Strip 11 moves onto the Take-up Wheel/Torsion Spring 12 by torsional spring force and thereby automatically moves forward and positions the next Unit Dose Blister. In addition, an Indexing Scroll 6 number ribbon is included that co-aligns with and winds in conjunction with the Unit Dose Blister Strip 11 to advance the number visible in the dose Counter Window 5.

Referring to FIG. 8, the Indexing Sprocket 13 is adapted for insertion over an Indexing Post 14 and includes a hole in the center and an outer generally cylindrical surface with Cavities 20 that key on and maintain alignment of the Unit Dose Blisters. The Indexing Sprocket 13 maintains positional synchronization with the Unit Dose Blister Strip 11 and by maintaining control of the rotation of the Indexing Sprocket 13, indexing and positioning of the Unit Dose Blisters is accomplished. A vertically disposed Indexing Post 14 extends through and is aligned substantially to the vertical axis of the Indexing Sprocket 13. The Indexing Post 14 is free to travel vertically and is attached and in contact with the Dispensing Button 3. When the Dispensing Button 3 is pivoted up from the storage position to the ready for dispensing position, the Indexing Post 14 moves vertically along the axis of the Indexing Sprocket 13. The Indexing Post 14 is affixed to the Dispensing Button 3 in a manner that prevents rotation of the Indexing Post 14 yet allows movement vertically with the Dispensing Button 3 position. Structures can be used to secure the Indexing Post 14 to the Dispensing Button 3 such as a pin attachment or the like that allows vertical movement with the Dispensing Button 3 position yet does not allow rotation of the Indexing Post 14. The Indexing Post 14 has nibs 21 that are slidably disposed in slots of the inner barrel of the Indexing Sprocket 13 and through this nib 21 engagement, the Indexing Post 14 can prevent or allow rotation of the Indexing Sprocket 13 in a controlled manner. While the barrel of the Indexing Sprocket 13 is generally circular in cross section, the inner barrel of the Indexing Sprocket 13 includes a surface on which the Indexing Post nibs 21 slide within grooves. The groove surface is recessed with regard to the sidewall and forms channels that the nibs 21 slidably fit within. Referring now to FIG. 8, affixed to and disposed inside the casing in this example, the inner barrel surface of the Indexing Sprocket includes grooves on its internal surface along with a flexible member 22 that deflects to allow the Indexing Post nibs 21 to travel past the flexible member 22 and along the corresponding vertical grooves in the Indexing Sprocket 13 thereby preventing rotation of the Indexing Sprocket 13 through the travel of the Dispensing Button 3 from the ready to dispense position to the storage or dispensed position.

Figure 9A:
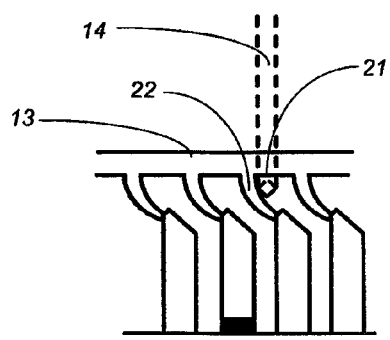
FIG. 9a through 9e is a diagram of the indexing grooves and action
Figure 9B:
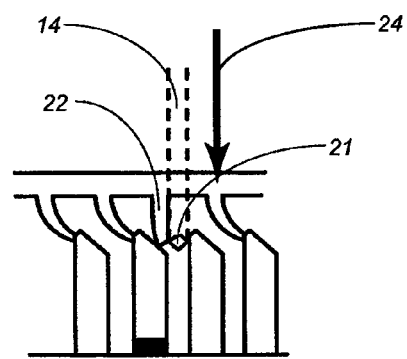
Figure 9C:
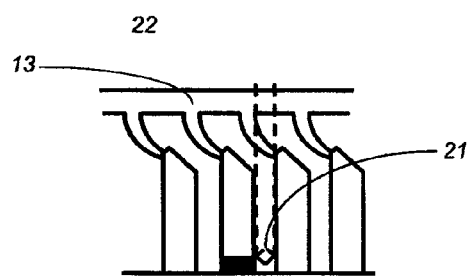
Figure 9D:
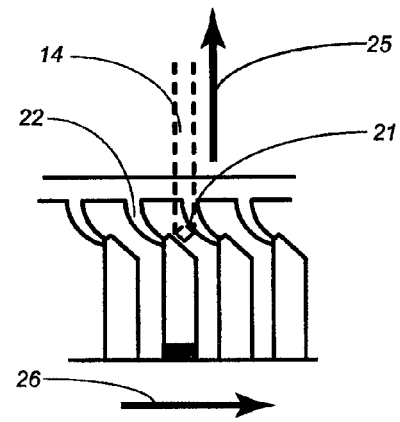
Figure 9E:
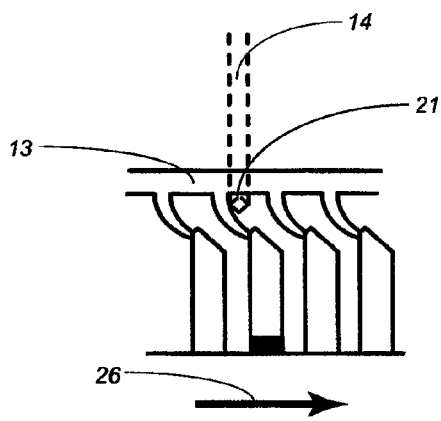

FIG. 9*a* through FIG. 9*e* is a depiction of the ratchet grooves of the Indexing Sprocket 13 and the nibs 21 on the Indexing Post 14 and are shown as if they were unrolled onto a flat surface and looking from the inside of the Indexing Sprocket 13. In FIG. 9*a* the flexible members 22 are disposed on the ends of the channels. As the Dispensing Button 3 moves the Index Post 14 down as in FIG. 9*b* arrow 24, the flexible member 22 allows the Index Post nibs 21 to pass into and along the groove without rotation of the Indexing Sprocket 13. As shown in FIG. 9*c*, the flexible member 22 returns to position and opens a secondary channel that is disposed generally perpendicular to the axis of the Indexing Sprocket 13. The Indexing Post nibs 21 move vertically along the slots as shown by arrow 25 to the top position when the Dispensing Button 3 is moved to the ready position as shown in FIG. 9*d*. This action allows the Indexing Sprocket 13 to rotate in a controlled manner when the nibs 21 align with the secondary channel above the next flexible member 22 and thereby allows the Indexing Sprocket 13 to rotate ⅙ turn per arrow 26 and stop in order to index the Unit Dose Blister Strip 11 forward to the next position as in FIG. 9*e*. In this position, the Indexing Sprocket 13 is ready for the next index cycle. Referring again to FIG. 6 the Take-up Wheel/Torsion Spring 12 has a hook that the Unit Dose Blister Strip 11 attaches to and is kept under constant winding tension and allows the Unit Dose Blister Strip 11 to wind around the Take-up Wheel/Torsion Spring 12 with the dispense and indexing cycle until all Unit Dose Blisters are dispensed. A pivoted Separator 23 shown with an accurate profile in FIG. 6 provides a barrier between the undispensed and dispensed Unit Dose Blister Strip 11 sections. As the spent Unit Dose Blister Strip 11 winds onto the Take-up Wheel/Torsion Spring 12 and unwinds from the cavity with the undispensed strip, the pivoted Separator 23 rotates about the pivot to accommodate the space needed for the dispensed Drug Form Blister Strip 11.

Figure 10:
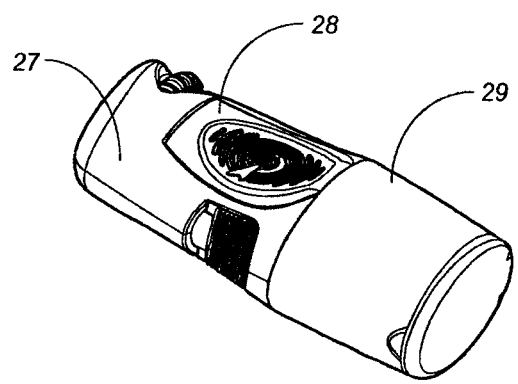
FIG. 10 is an illustration of a preferred embodiment of an ophthalmic delivery system.
Figure 11:
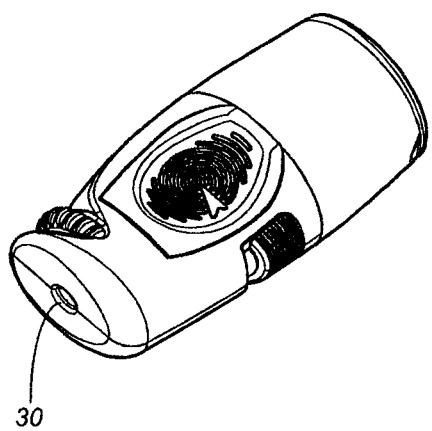
FIG. 11 is an illustration of a preferred embodiment from the bottom showing the dose window.

An alternative embodiment of an ophthalmic delivery system is shown in FIGS. 10-21*b*. This embodiment is shown in storage configuration FIG. 10 and FIG. 11. The delivery system as shown is a lever button cartridge embodiment of an ophthalmic delivery system. The embodiment as shown in FIG. 12 includes a body 27, button lever 28, and storage cap 29. The delivery system in FIG. 10 is in storage mode as can be seen with the storage cap 29 in place with the button lever 26 in a closed position. The button lever 26 is held in the closed position by the storage cap 29 and is locked in this position by retention of the end of the button lever 26 fitting under the edge of the storage cap 29 when in place. This embodiment of an ophthalmic drug delivery system is also shown in FIG. 11 and shows the delivery system in storage mode and shows the dose indicator window 30. When the storage cap 29 is removed from the body 27, the button lever 28 raises from spring force into the ready position as shown in FIG. 12.

Figure 14:
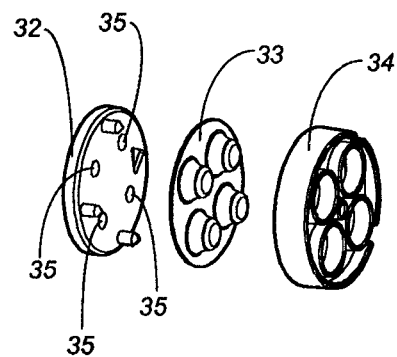
FIG. 14 is a detail of the components that make up the replaceable drug cartridge.
Figure 15:
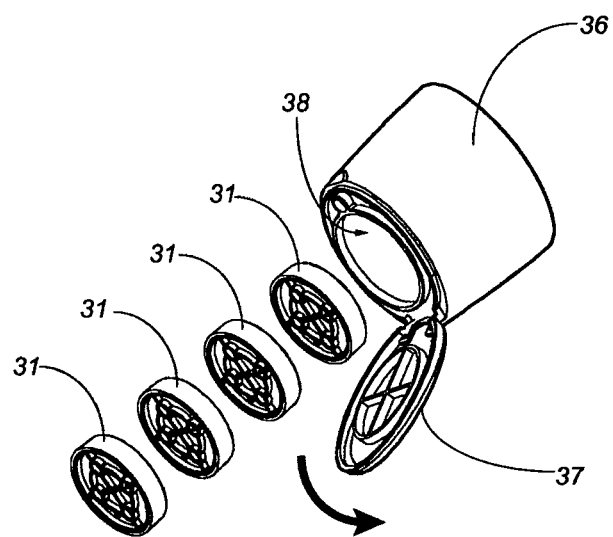
FIG. 15 is an illustration of the Storage Cap.

This delivery system embodiment includes a drug cartridge consisting of several drug dose forms. The delivery system in the drawings provides four doses in the cartridge disk, but it is understood that more or fewer drug forms can be provided in the same or a similar cartridge as needed. The assembled drug cartridge 31 is shown in FIG. 13*a* and FIG. 13*b*. The drug cartridge consists of a disk with four drug forms with internal piercer as disclosed in patent disclosure U.S. application Ser. No. 11/114,251, which is incorporated in its entirety herein. The components comprising the drug cartridge are shown in FIG. 14 and consist of the cartridge top 32, drug form disk 33, and cartridge bottom 34. These components are assembled and sealed into an assembly and together make up the drug cartridge 31. The drug cartridge top 32 includes drug discharge ports 35 that are aligned with the drug containing forms in the drug disk 33. These drug discharge ports 35 provide support and an opening for the operation of the internal piercing nozzle as disclosed in U.S. application Ser. No. 11/114,251 and included herein. The Storage cap 29 is shown is FIG. 15 and consists of a storage cap body 36 and cover 37 and is shown with the cover 37 open. The storage cap cover 37 is rotated up and exposes a circular storage volume 38. This storage volume 38 allows drug cartridges 27 to be stored for use in the delivery system.

Figure 16:
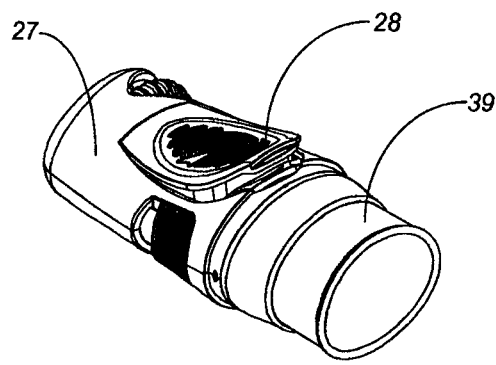
FIG. 16 is an illustration of the delivery system ready for dispensing.
Figure 17:
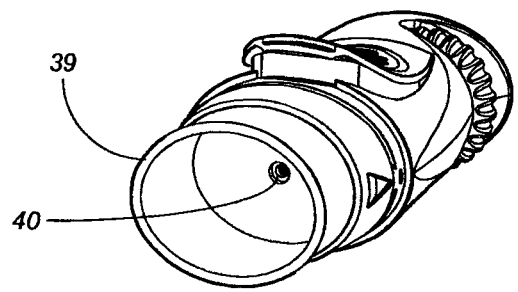
FIG. 17 is an illustration of the preferred embodiment delivery system front view showing the drug discharge port.
Figure 18A:
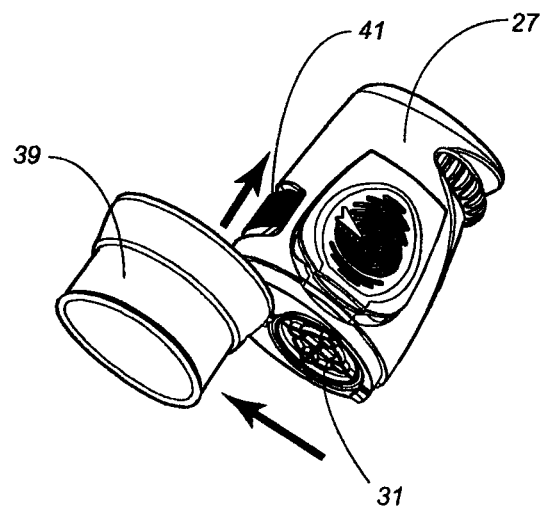
FIG. 18a and FIG. 18b are illustrations showing the delivery system with the eye cup opened for replacement of the drug cartridge.
Figure 18B:
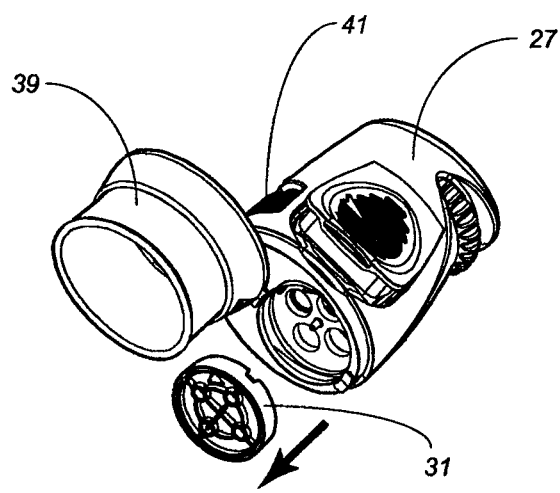

The delivery system is shown in FIG. 16 with the storage cap 29 removed and in a ready for use configuration. The front oval portion forms the eye cup 39 and is placed to the eye to align and position the delivery system for dispensing the drug into the eye by pressing the lever button 28. The drug is dispensed from the drug discharge port 40 in FIG. 17 in the center back wall of the eye cup 39. The delivery system is shown in the drug cartridge reload position in FIG. 18*a* and FIG. 18*b*. In order to replace or load the drug cartridge in the delivery system, the eye cup 39 is able to slide over to clear the area that holds the removable drug cartridge 31. To release the eye cup 39 to slide into the reload position, the eye cup release button 41 is moved down as shown in FIG. 18*a*. When the eye cup 39 is in the reload position the drug cartridge 31 may be removed and replaced as shown in FIG. 18*b*. When the drug cartridge 31 is in place in body 27, the eye cup 39 is repositioned into its normal operating position.

Figure 19:
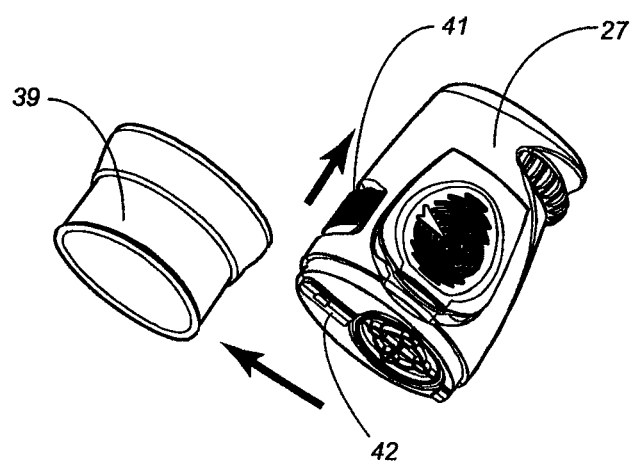
FIG. 19 is an illustration of removal of the eye cup from the delivery system.
Figure 20:
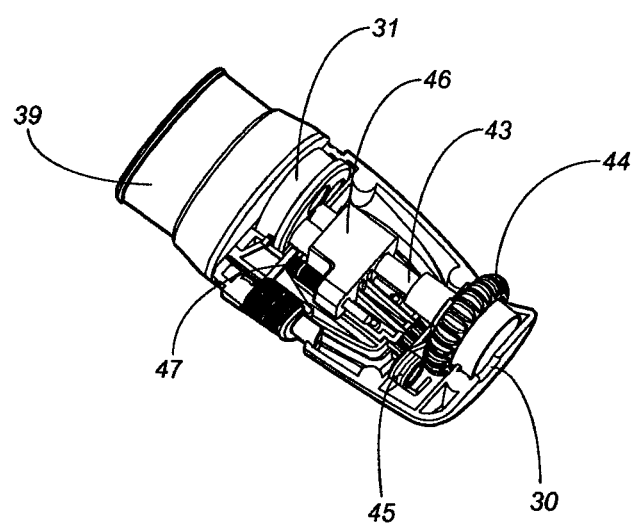
FIG. 20 is an illustration of internal components of the delivery system with the top body removed.

The eye cup 39 is completely removable by pressing eye cup release button 41 down and holding while moving the eye cup 39 to the side on tongue and groove track 42. This allows cleaning or replacement of the eye cup 39 as shown in FIG. 19. FIG. 20 shows the delivery system with internal components exposed. The drug cartridge 31 has several drug forms. These drug forms are positioned into a dispensing position by rotating the drug cartridge 31 such that the drug forms align with the eye cup 39 center. After a drug cartridge 31 is dispensed, the delivery system is able to index the drug cartridge 31 to the next drug form and this is done by engaging the drug cartridge 31 with index shaft 43 such that the rotation of the index shaft 43 rotates the drug cartridge 31. Index knob 44 is attached to the index shaft 43. Rotating the index knob 44 rotates the drug cartridge 31 and allows positioning of the drug form for dispensing and incremental positioning detents are provided by the detent spring 45 to indicate correct alignment of the drug form for dispensing. In addition, by placing numbers on the index knob 44 in locations corresponding to the drug form location rotationally in the drug cartridge 31, the number for that dose shows through the dose indicator window 30.

The mechanism in this delivery system for dispensing the drug form includes a sliding piston 46, return spring 47 shown in FIG. 20. In addition, the dispensing mechanism is shown in cross section, FIG. 21*a* and FIG. 21*b*. These cross sections show the interaction of the lever dispensing button 28 and the sliding piston 46. Cartridge 31 is positioned rotationally with a drug dispensing form aligned with the dispensing nozzle 40 in FIG. 17 and the piston end of the sliding piston 46. The return spring 47 pushes against the sliding piston 46 keeping it in a retracted position. Piston 46 has a cam surface 48 that interacts with the cam surface 49 on the lever button 28 as shown in cross section FIG. 21*a*. When Button 28 is pressed, the button rotates on the button pivot 50 and the cam surface 49 presses against the cam surface 48 of piston 46 thereby imposing a force in the forward direction. This moves the sliding piston 46 against the drug form contained in drug cartridge 31 thereby dispensing the drug through the dispensing nozzle 40 in a stream 51 shown in FIG. 21*b* towards the eye positioned in front of the eye cup 39. This is the complete dispensing action and the position of the piston 46 and the Button 28 is shown in FIG. 21*b* after dispensing, the button 28 can be held in place and the storage cap 29 replaced and thereby holding the button 28 in the storage position as shown in FIG. 10 and FIG. 11. If additional dispensing is needed prior to storage, the button 28 is released and spring force from return spring 47 pushes the sliding piston 46 back and thereby transmits force to the cam surfaces and lifts the button 28 into the ready position again. At this point, the rotation knob 44 in FIG. 20 may be rotated to the next detent provided by detent spring 45 and rotationally position the drug cartridge 31 to a new drug form for dispensing.

Figure 21A:
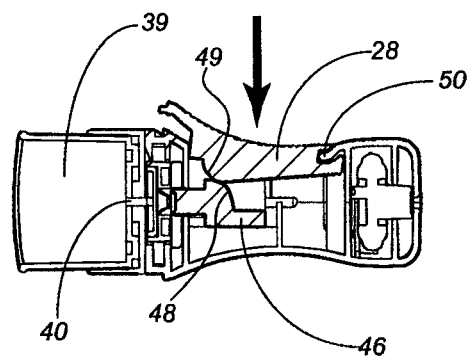
FIG. 21a and FIG. 21b are cross section views of the delivery system showing the action of the dispensing mechanism.
Figure 21B:
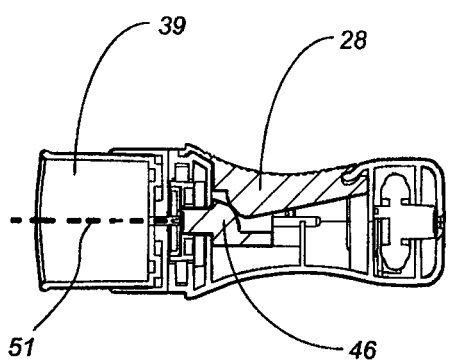

In FIG. 21*a* cross section, the interaction of the cam surfaces 48 and 49 is shown. By varying the angle of interaction of the cam surface 49 on button 38 and the cam surface 48 on sliding piston 46, the force transmitted from the button 28 to the sliding piston 46 may be controlled. This relative angle results in a force vector that can be varied as the position of the button 28 changes thereby providing a mechanical advantage or disadvantage to the force transmitted from the button 28 to the sliding piston 46 and provide the ability to control the force transmitted from the button 28 to the sliding piston 46 that crushes the drug dispensing form and dispenses the drug.

Figure 22:
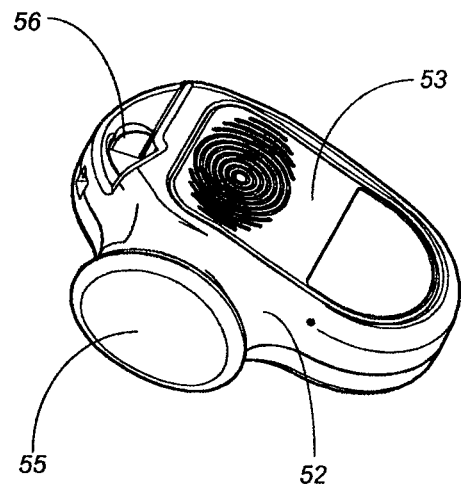
FIG. 22 is an illustration of another preferred embodiment of a disposable ophthalmic delivery system with multiple doses and integrated eye cup.

In another embodiment of the delivery system, the unit is disposable and contains a factory loaded strip of drug forms for dispensing. This embodiment is shown in FIG. 22. This embodiment of the delivery system is shown in storage or transport mode and has a body 52 and a dispensing paddle button 53. This embodiment does not have a separate eye cup. Instead, it is integrated with the body 52. A removable cap 55 covers the area of the body that functions as an eye cup. For ease of transport, when the delivery system is in this mode, the paddle button 53 is positioned flat and flush with body 52. Also shown in this view is the indexing lever 56.

Figure 23:
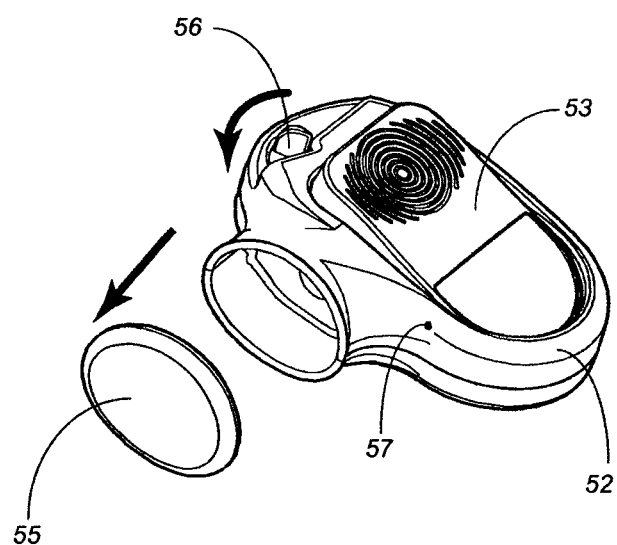
FIG. 23 is an illustration of the delivery system with the cap removed and ready for dispensing.

FIG. 23 shows the delivery system with the eyecup cap 55 removed and the position of the dispensing paddle button 53 after actuating the indexing lever 56. When index lever 56 is pushed forward and returned, the paddle button 53 lifts up and rotates about the pivot 57 and the next drug form dose is positioned for dispensing.

The paddle button 53 and upper half of body 52 have been removed in FIG. 24 to reveal part of the internal mechanism of the delivery system. A coiled dosage blister strip 57 is wound around a feed wheel 58 and in engagement with the indexing wheel 59 such that advancing this mechanism requires the index lever 56 to be pushed through its full travel to engage the indexing wheel 59 such that the feed-wheel 58 rotates when the indexing wheel and lever returns to its starting position by the force provided by the torsion spring 60. This rotation of the feed wheel 58, feeds the blister strip 57 and the next dose form blister on the dose form strip 57 to a position between the piston 61 and the discharge port 62. As can be seen in FIG. 23, the button tilts up to the ready position around pivot point 63. As the button is depressed, the paddle button 53 drives the piston 61 into the dosage form strip 57, crushing the blister and dispensing the dose through the discharge port 62. In this embodiment, the length of the paddle button 53 provides a mechanical advantage to a user to create sufficient force to crush the dosage form and produce the desired spray or stream pattern. After the dosage has been dispensed, the paddle button 53 comes to rest in the storage position.

Figure 26:
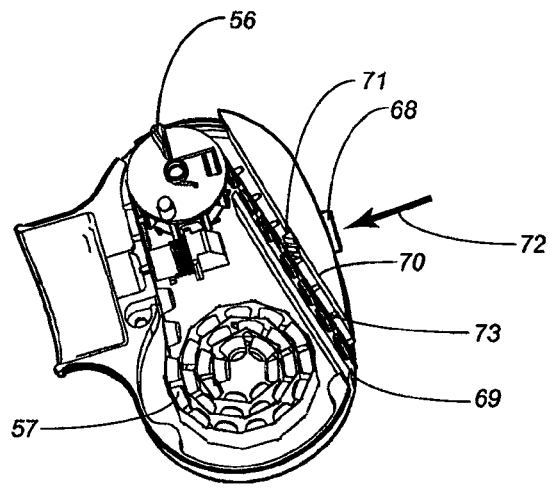
FIG. 26 is a drawing showing the drug form strip cutoff and disposal mechanism.

The previous embodiment stores the dose form blister strip 57 internally to the body of the delivery system and as the dose form strip 57 is advanced, the spent strip accumulates inside the body until the doses are completely used and the entire delivery system is disposed of. A modification of this previous embodiment is the addition of a cutting and temporary dose form storage zone in the body of the delivery system. FIG. 25*a* and FIG. 25*b* shows this embodiment of the delivery system with the addition of a cut-off button 68 and exit port 69. After the dose form blister is crushed, the drug form strip 57 continues to index forward. As the index lever 56 is indexed to the next dose and dispensed, the dose form strip 57 moves towards the exit port 69. FIG. 26 shows the delivery system with the paddle button 53 and top half of the body removed. When between one and four doses are indexed by the index lever 56, exhausted forms on the drug form strip 57 will move into the storage zone 70 past the cutter 71. When the user chooses to dispense the exhausted dose blisters on the dose form strip 57, pressing the cut-off button 68 in the direction of arrow 72 will cut and separate the dose form strip 57 and the exhausted blisters on the far side of the cutter 68 and will drop through exit port 69 in direction of arrow 73 from the delivery system for disposal. This cut off capability and mechanism allows the user to dispense up to four doses of expended blisters on the drug form strip 57 to be contained within the delivery system in the storage zone 70 and elect to dispose of the portion of the dose form strip past the cut off blade 71 by pressing the cut off button 68.

Figure 27:
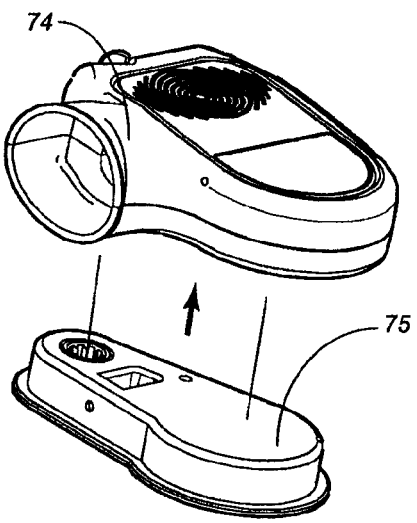
FIG. 27 is an illustration of an embodiment of an ophthalmic delivery system with a replaceable cartridge of drug form strips.
Figure 28:
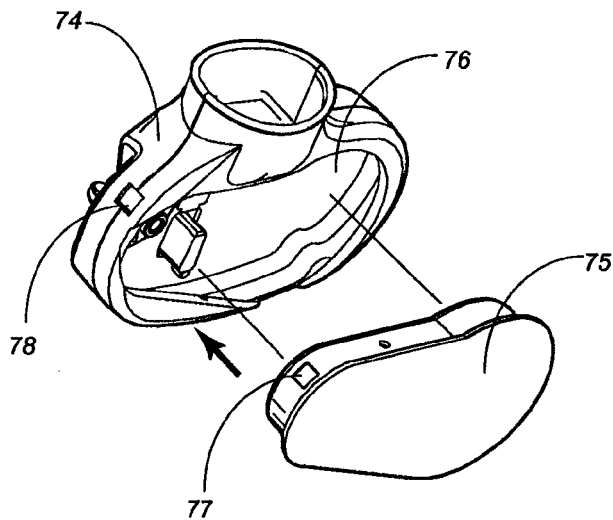
FIG. 28 is an illustration showing the placement of the replaceable drug form strip cartridge.

Another embodiment of the delivery system is illustrated in FIG. 27 and FIG. 28. This embodiment is also designed to dispense multiple dosages and include all functions of the previous embodiments, however, this delivery system is designed to use a replaceable cartridge containing the drug form strip and indexing mechanism shown in FIG. 22-26. Consequently, the internal views of this embodiment are not shown. This embodiment of the dispensing delivery system shown in FIG. 27 and FIG. 28 includes a body 74 modified to accept cartridge 75. FIG. 28 shows the delivery system body 74 containing a cavity 76 to accept the cartridge 75. A dosage window 77 is also present on the delivery system replaceable drug cartridge 75 with indicator numbers to inform a user of the number of doses remaining in the delivery system and shows through the window opening 78 in the delivery system body 74. Functions of this embodiment are the same as the previous embodiment except these described modifications allow the drug doses to be contained within a replaceable cartridge.

Figure 29:
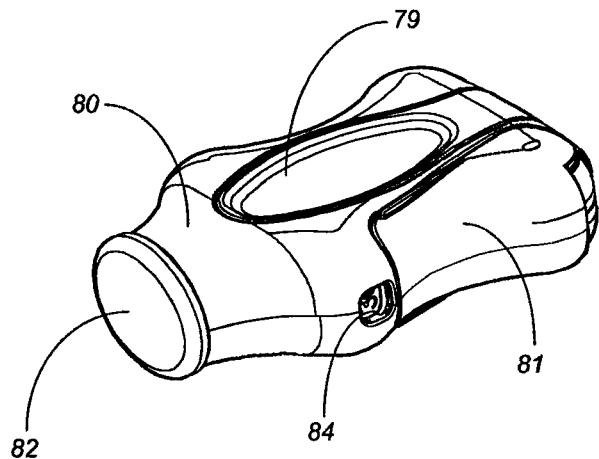
FIG. 29 is an illustration of another embodiment of the delivery system specifically for individuals with limited motor skills or capability.
Figure 30:
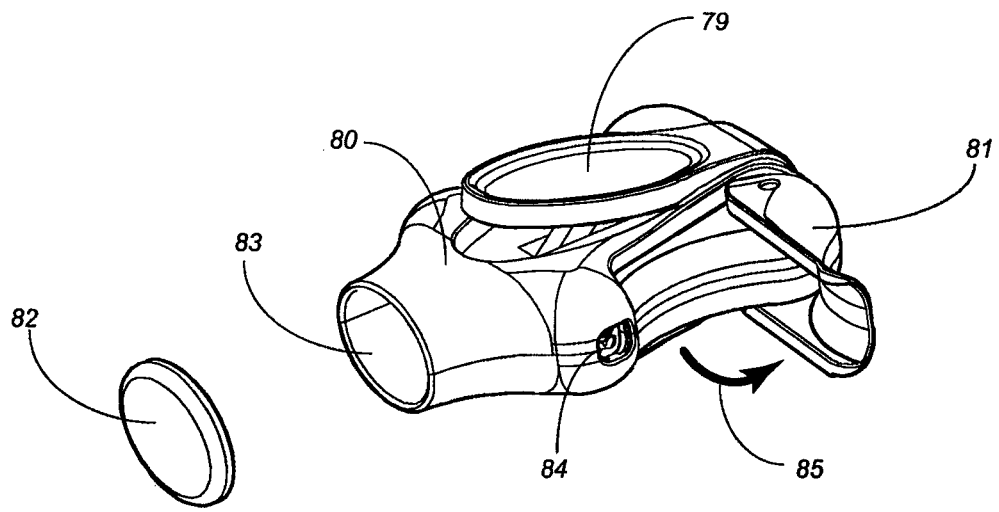
FIG. 30 is an illustration of the delivery system with the cap removed and the action of the indexing lever shown.
Figure 31:
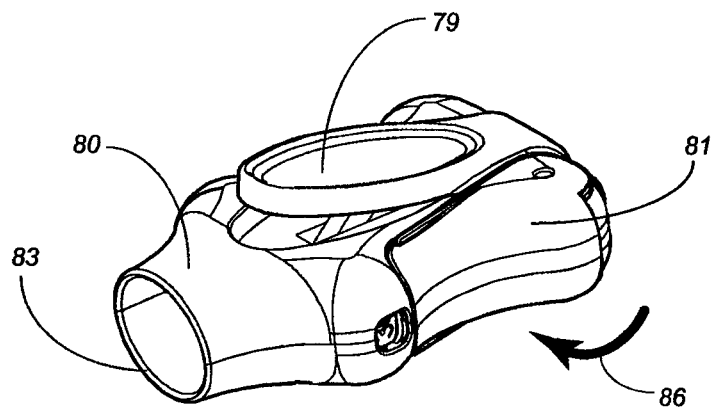
FIG. 31 is an illustration of the delivery system ready for dispensing.

Another embodiment of the ophthalmic delivery system is configured for use by persons with limited dexterity or reduced motor skills. This embodiment has an integrated eye cup in the body of the delivery system and contains a drug form strip that is not replaceable as in previous embodiments. This embodiment as shown in FIG. 29 and FIG. 30 and the body is larger. This allows easier handling and includes a large dispensing lever button 79. The internal mechanism is similar to the previous embodiments. Consequently, the internal views of this embodiment are not shown. The dispensing delivery system includes a body 80, and a lever button 79 on the top surface thereof and a large indexing lever 81 for advancing the dosages into the dispensing position. This embodiment further includes an easy to remove cap 82 that covers the integrated eye cup 83 during storage. A larger and easy to read dosage window 84 is also present on the delivery system with indicator numbers to inform a user of the number of doses remaining in the delivery system. The sequence of action of this embodiment is to remove the cap 82, pull index lever 81 out as shown by arrow 85 and then back to the storage position as shown in FIG. 31 by arrow 86. This causes the internal mechanism to bring a new drug form into the dispense position and raises the dispense button 79 as in other embodiments. This places the delivery system into the ready mode for dispensing. The delivery system with eye cup 83 placed to the eye and the dispense button 79 is pressed to dispense the drug. The delivery system is ready for storage when the cap 56 (FIG. 30) is replaced.

Figure 32:
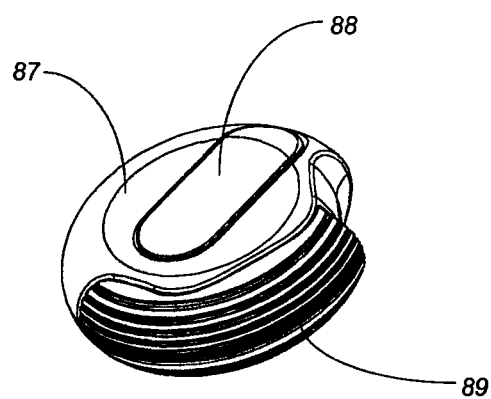
FIG. 32 is an illustration of another embodiment of the delivery system designed to be compact.
Figure 33:
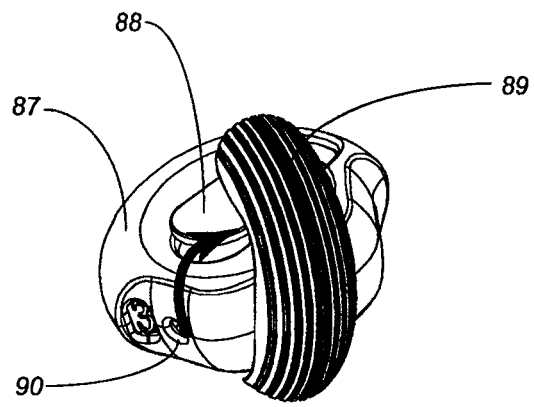
FIG. 33 is an illustration showing the action of the combined index lever and cover.
Figure 34:
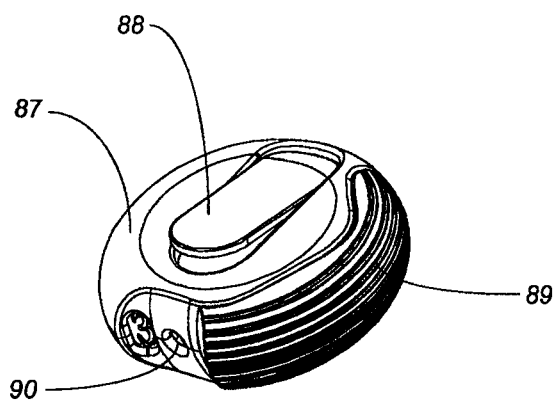
FIG. 34 is an illustration of this embodiment of the delivery system ready for dispensing.

Certain embodiments of personal delivery systems described herein include the device body without an eye cup. The delivery system is held in front of the eye and dispenses a dose in a stream when the dispensing button is pressed. The internal mechanisms of this embodiment include the unit dose strip, piston and dispensing details functionally the same as shown in previous embodiments. Consequently, the internal components of this embodiment are not shown. This embodiment is shown in FIG. 32 in a storage configuration. The delivery system includes the body 87, a dispensing button 88, and a combined index/cover 89. To open the delivery system and put into the dispense mode as in other embodiments, the index/cover 89 is rotated 180 degrees from the storage position into the dispense position. This action of rotating the index cover is shown in FIG. 33 and FIG. 34 and performs the same function of indexing as in previous embodiments and is used to advance a dosage blister or unit dosage form to a position adjacent a piston and also uncovers the discharge port 90, ready for dispensing by pressing button 88. In the ready position as shown in FIG. 34, depressing the dispense button 88 causes the piston to crush the unit dosage form and dispense the fluid from discharge port 90 contained therein. After dispensing, the index/cover 89 is rotated back into the storage position as shown in FIG. 32.

Figure 35B:
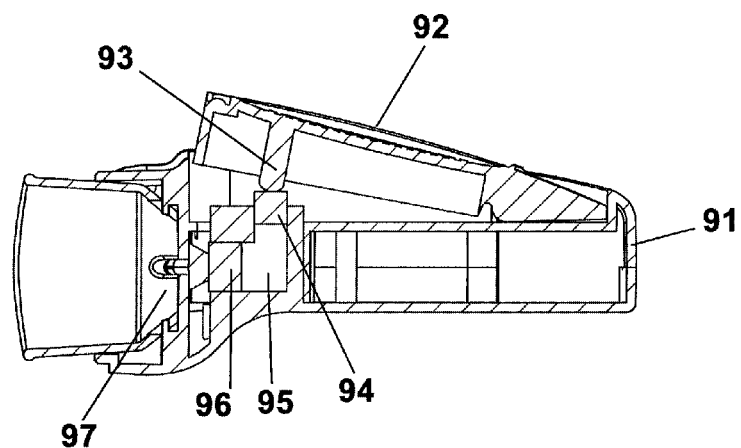
FIGS. 35A and 35B is an illustration of an embodiment in which a mechanical force is translated to a pneumatic or hydraulic force to dispense the dosage form contents.
Figure 35A:
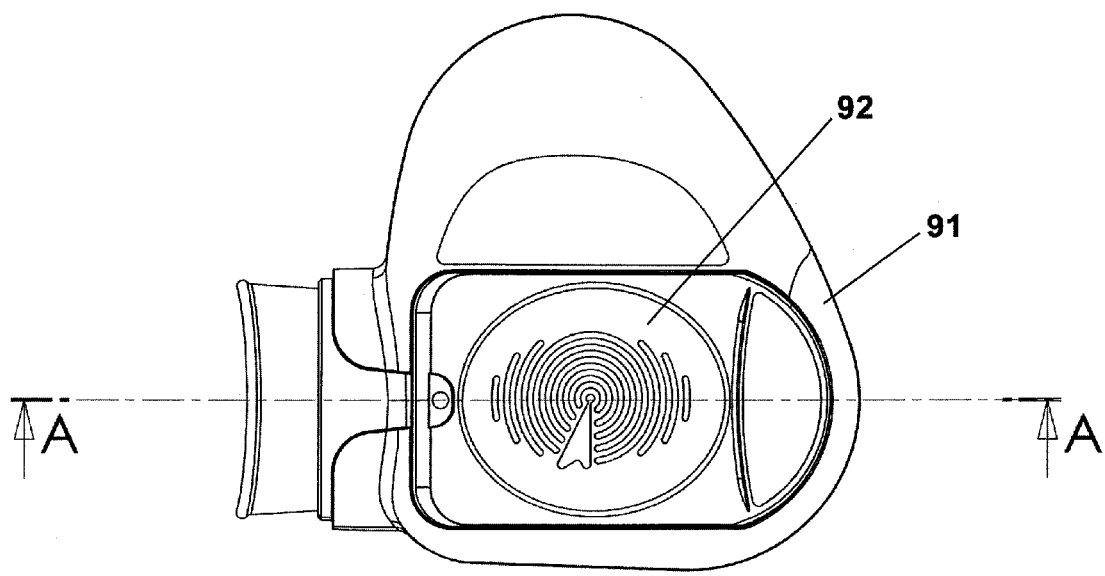

In certain embodiments, a personal delivery system as disclosed herein can include a mechanism in which a pneumatic or hydraulic force is used to drive dispensing of the contents of a dosage form. An embodiment of such a device is shown in FIGS. 35A and 35B. This embodiment includes a body 91 and a dispensing button or paddle 92. The section view in FIG. 35B shows that the paddle 92 includes a projection or arm 93 that contacts a first piston 94 when in the ready position. Pressing the paddle or button drives the first piston into a chamber 95 that is filled with a compressible gas or liquid. The compression in the chamber then drives a second piston 96 into a dosage form, crushing it and dispensing the contents.

Figure 36B:
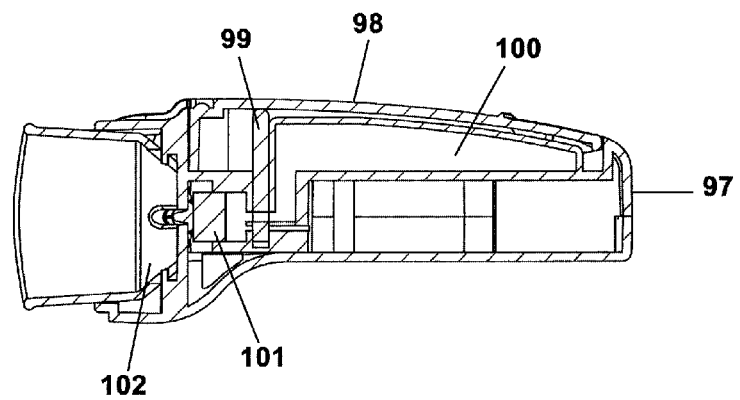
FIG. 36A-36C is an illustration of an embodiment in which a compressed gas is used to dispense the contents of the dosage form.
Figure 36A:
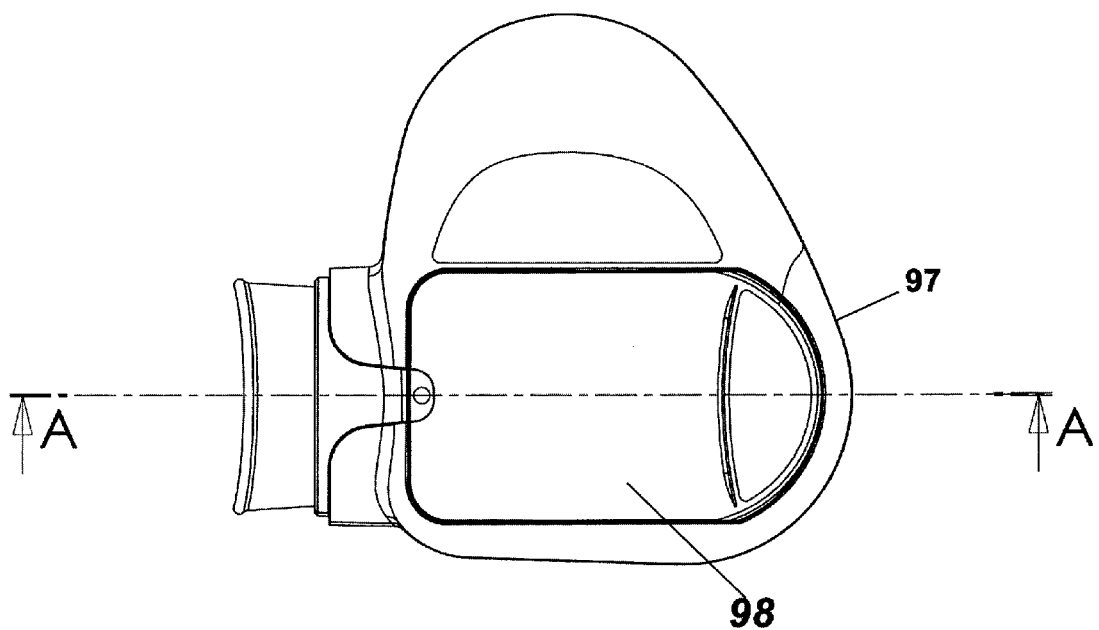
Figure 36C:
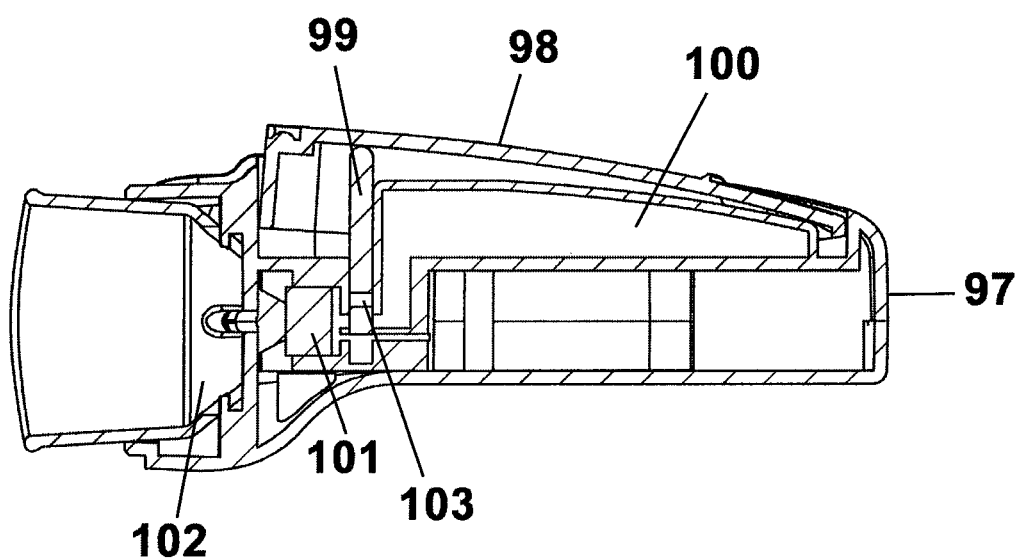

Certain embodiments of the disclosure can also include a mechanism in which compressed gas is used to drive a plunger into a dosage form as disclosed herein. An example of such a device is shown in FIG. 36A-36C. The device as shown includes a body 97 and button 98 for dispensing a dose from the device. A rod 99 attached to the bottom side of the button is forced downward when the button is pressed, aligning a pore 103 with a chamber 100 that contains the compressed gas. As the pore aligns with the opening to the chamber, gas is released forcing piston 101 into the dosage form 102, thus crushing the blister or ampoule and dispensing the contents.

It is a further aspect of the disclosure that any of the described dispensing delivery systems can be battery powered, utilizing a motorized piston, cam or screw-drive plunger as the primary mechanism of action for firing the delivery system. The delivery systems may be powered by conventional disposable batteries or by rechargeable batteries or any other appropriate power system. The control systems in the delivery systems for the safety mechanism, trigger, unit dosage form indexing release and delivery system status reporting can be electronically controlled by a programmable microprocessor computer delivery system such as a PCB or alternatively an ASIC located in the delivery system. A visual display panel with control buttons can serve as an interface for the user to operate and even program the delivery system.

In certain embodiments, the delivery system motor is a DC powered step motor or servo motor or custom motor with internal gearbox requiring 3 to 9 volts, with a torque of 40 to 120 oz-in and speed equaling 50 to 240 rpm. It is understood by those of skill in the art that this motor description is exemplary only and that other appropriate motors well known to those in the art could be used with the delivery system, or other delivery systems disclosed herein.

The firing mechanism of the delivery systems can include a step or servo style DC motor connected to a screw-drive via a gearbox. The motorized screw-drive operates at high speed to drive a piston against the unit dosage form to fire the delivery system and then retracts the piston to a start position. Alternatively, the mechanism can include a motorized cam actuated piston or a motorized cam/spring driven piston. In the case of a motorized cam actuated piston, the motor rotates a cam directly connected to the piston to provide compressive force. In the case of a motorized cam/spring the motor actuates a cam, which cocks a spring connected to the piston. When the spring is released either mechanically or electronically, it provides the compressive force for the piston to fire the unit dosage form.

In certain embodiments, any of the delivery systems disclosed herein can incorporate a control system consisting of a Printed Circuit Board ("PCB") or alternatively an Application Specific Integrated Circuit ("ASIC"), or other electronic control systems known in the art, preferably sealed in the delivery system. The control system can perform the following functions:

On/Off device activation
LCD Display and Device Status Monitor
Electronic Trigger
Indexing Safety Release The control system may be designed to monitor and report device status including, but not limited to:

Drug Administration Sequence
Compliance Notification and Tracking
Drug Identification and Expiration Tracking
Device Operational and Lifecycle Status
Drug Expiry Status
Automated wireless prescription refill/reorder
Compliance History Preferably, the PCB (or alternatively the ASIC) in the delivery system utilizes a combination of firmware, software, and non-volatile memory to operate the delivery system, for tracking and reporting on delivery system status and user compliance.

All of the systems, compositions and/or methods disclosed and claimed herein can be made and executed without undue experimentation in light of the present disclosure. While the systems, compositions and methods of this disclosure have been described in terms of certain embodiments, it will be apparent to those of skill in the art that variations may be applied to the systems, compositions and/or methods and in the steps or in the sequence of steps of the method described herein without departing from the concept, spirit and scope of the disclosure. More specifically, it will be apparent that certain physical structures may be substituted for the physical structures described herein and the same or similar results would be achieved. All such similar substitutes and modifications apparent to those skilled in the art are deemed to be within the spirit, scope and concept of the disclosure as defined by the appended claims.

What is claimed is:

1. A drug delivery system comprising:
   a housing configured to contain one or more crushable unit dosage forms;
   a user activation mechanism, effective when activated, to engage a drug delivery mechanism comprising a piston drivable into at least one dosage form contained in the housing, wherein the activation mechanism provides a mechanical advantage, a mechanical disadvantage or a combination of mechanical advantage and disadvantage to the activation mechanism; and
   a discharge port formed in or contiguous with the housing and configured to release the contents of a dosage form upon activation of the activation mechanism.

2. The drug delivery system of claim 1, wherein the dosage forms are blisters comprising a piercable region and an internal piercing mechanism, wherein, the piercing mechanism comprises an internal channel positioned to release the content of the blister through the piercing mechanism in a spray, stream, or mist pattern and out the discharge port when the blister is crushed and the piercing mechanism pierces the piercable region.

3. The drug delivery system of claim 1, wherein the housing is configured to contain multiple dosage forms, and wherein the drug delivery system further comprises a mechanism to sequentially position a dosage form adjacent the dispensing channel and optionally to simultaneously advance a spent dosage form away from the dispensing channel.

4. The drug delivery system of claim 3, wherein the housing is configured to accept a cartridge containing one or more blister dosage forms and to position the dosage forms in dispensing position.

5. The drug delivery system of claim 4, wherein the housing is configured to accept a cartridge containing a single dosage form.

6. The drug delivery system of claim 4, wherein the housing is configured to accept a cartridge containing a plurality of dosage forms contained on a disc, a ring or a strip.

7. The drug delivery system of claim 6, comprising an indexing wheel knob connected to an indexing lever configured such that activating the indexing knob advances a unit dosage form into dispensing position.

8. The drug delivery system of claim 6, wherein the housing comprises a winding take-up wheel/torsion spring in engagement with an indexing sprocket attachable to a strip of blister dosage forms.

9. The drug delivery system of claim 4, wherein the housing is configured to accept a rotatable disc or ring containing a plurality of blister dosage forms.

10. The drug delivery system of claim 1, wherein the activation mechanism provides a mechanical disadvantage such that a pre-defined minimum threshold force must be applied to the activation mechanism in order to active a drug delivery mechanism.

11. The drug delivery system of claim 1, wherein the activation mechanism provides a mechanical advantage such that, when activated the force driving the piston into the dosage form is greater than the simultaneous force applied to the activating mechanism.

12. The drug delivery system of claim 1, wherein the activation mechanism comprises a hinge, spring, cam, or motorized drive.

13. The drug delivery system of claim 1, wherein the mechanically advantaged or disadvantaged mechanism comprises a lever, cam or an inclined plane.

14. The drug delivery system of claim 13, wherein a mechanical advantage or disadvantage is provided by an interaction of an angled face on an activation button and an angled face on a piston.

15. The drug delivery system of claim 13, wherein a mechanical advantage or disadvantage is provided by an interaction of an arcuate face on an activation button and an arcuate face on a piston.

16. The drug delivery system of claim 13, wherein the activation mechanism provides for a mechanical disadvantage during first stage of activation until a minimum threshold force is exerted and a mechanical advantage during a second stage of activation during which a piston is driven into a dosage form.

17. The drug delivery system of claim 2, wherein the dosage form contains a substance comprising an active pharmaceutical ingredient or biologic.

18. The drug delivery system of claim 17, wherein the substance is preservative-free.

19. The drug delivery system of claim 17, wherein the substance is dispensed as a drop, droplet, stream or spray upon release from the unit dosage form.

20. The drug delivery system of claim 17, wherein the substance is sterile until released from the unit dosage form.

21. The drug delivery system of claim 17, wherein the unit dosage forms further comprises a head space of gas or air.

22. The drug delivery system of claim 1, further comprising a delivery device configured to deliver the contents of a dosage form to a selected body part of a drug recipient.

23. The drug delivery system of claim 22, wherein the delivery system is designed to deliver a dosage of drug into to the eye, nose, mouth, ear, or rectum of a recipient.

24. The drug delivery system of claim 22, wherein the delivery device is an eyecup.

25. The drug delivery system of claim 22, wherein the delivery device further comprises a detachable cap.

26. The drug delivery system of claim 25, wherein the cap is configured as a storage device for dosage form containing cartridges.

27. The drug delivery system of claim 1, wherein the delivery system further comprises a programmable microprocessor.

28. The drug delivery system of claim 27, wherein the programmable microprocessor is a Printed Circuit Board or an Application Specific Integrated Circuit coupled to visual display interface and audible notification system.

29. The drug delivery system of claim 27, wherein the visual display interface is a Liquid Crystal Display or Light Emitting Diodes.

30. An ophthalmic drug delivery system comprising:
   a housing configured to contain one or more crushable unit dosage forms;
   a user activation mechanism, effective when activated, to engage a drug delivery mechanism comprising a piston drivable into at least one dosage form contained in the housing, wherein the activation mechanism provides a mechanical advantage, a mechanical disadvantage or a combination of mechanical advantage and disadvantage to the activation mechanism;

a discharge port formed in or contiguous with the housing and configured to release the contents of a dosage form upon activation of the activation mechanism; and an eye cup attached to the housing disposed to direct the contents of the dosage form into the eye of a recipient.

31. The ophthalmic drug delivery system of claim 30, further comprising one or more unit dosage forms contained in the housing, wherein the dosage forms are blisters comprising a piercable region and an internal piercing mechanism, wherein, the piercing mechanism comprises an internal channel positioned to release the content of the blister through the piercing mechanism in a spray, stream, or mist pattern and out the discharge port when the blister is crushed and the piercing mechanism pierces the piercable region.

32. The ophthalmic drug delivery system of claim 31, wherein the dosage forms are contained in a cartridge.

33. The ophthalmic drug delivery system of claim 32, wherein the cartridge contains a plurality of unit dosage blisters configured on a strip, disk or ring, and further wherein the housing contains an indexing wheel connected to an indexing lever configured such that activating the indexing knob advances a unit dosage form into dispensing position.

34. The drug delivery system of claim 30, wherein the activation mechanism provides a mechanical disadvantage such that a pre-defined minimum threshold force must be applied to the activation mechanism in order to active a drug delivery mechanism.

35. The drug delivery system of claim 30, wherein the activation mechanism provides a mechanical advantage such that, when activated the force driving the piston into the dosage form is greater than the simultaneous force applied to the activating mechanism.

36. The drug delivery system of claim 30, wherein the activation mechanism comprises a hinge, spring, cam, or motorized drive.

37. The drug delivery system of claim 30, wherein the mechanically advantaged or disadvantaged mechanism comprises a lever, cam or an inclined plane.

38. The drug delivery system of claim 37, wherein a mechanical advantage or disadvantage is provided by an interaction of an angled face on an activation button and an angled face on a piston.

39. The drug delivery system of claim 37, wherein a mechanical advantage or disadvantage is provided by an interaction of an arcuate face on an activation button and an arcuate face on a piston.

40. The drug delivery system of claim 37, wherein the activation mechanism provides for a mechanical disadvantage during first stage of activation until a minimum threshold force is exerted and a mechanical advantage during a second stage of activation during which a piston is driven into a dosage form.

41. The drug delivery system of claim 32, wherein the unit dosage form cartridge comprises one or more aids for administering the unit dosage forms to a user selected from the group consisting of numbering, color coding, icon system coding, Braille, bar coding, and Radio Frequency Identification Device.

42. A drug delivery system comprising:

a housing;

a button on a surface of the housing and pivotable indexing lever that acts as a cover and an indexing lever from a closed position to a dispense position;

a firing mechanism comprising a piston connected to a link contained in the housing and in contact with the button through the link;

a discharge port attached to the housing and in fluid communication with a unit dosage form dispensing position in the housing; and a feed mechanism for a blister strip contained in the housing, and comprising a feed wheel, an indexing wheel, and a take-up wheel, effective to sequentially move unit dosage forms contained on the blister strip into dispensing position in front of the discharge port by turning the indexing wheel;

wherein when the dispensing button is in the raised position, depressing the button forces the piston into an unit dosage form in the dispensing position, thereby forcing the contents of the unit dosage form through the discharge port into the eye, and wherein the link provides a mechanical advantage to the piston.

43. The drug delivery system of claim 42, wherein the link comprises an inclined plane cam or a lever.

44. The drug delivery system of claim 42, wherein the blister strip comprises a plurality of internally pierced unit dosage forms.

45. The drug delivery system of claim 42, comprising an indicator connected to the indexing wheel and visible from outside the housing, wherein the indicator comprises symbols to indicate the number of unused unit dosage forms on a blister strip.

46. The drug delivery system of claim 42, wherein the symbols are numbers, letters, colors, or a combination thereof.

47. The drug delivery system of claim 42, wherein the indexing mechanism comprises a rotating lever.

48. The drug delivery system of claim 42, wherein the indexing mechanism comprises a rotating lever that also acts as a cover to the drug discharge area.

49. The drug delivery system of claim 42, comprising an indicator port adjacent to the discharge port positioned to reveal dosage counter indicators on the delivery system when viewed from the exterior of the housing.

* * * * *